US011564829B2

(12) United States Patent
Sharma

(10) Patent No.: US 11,564,829 B2
(45) Date of Patent: Jan. 31, 2023

(54) DEVICES FOR TREATING OBSTRUCTIVE SLEEP APNEA

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 479 days.

(21) Appl. No.: 16/752,614

(22) Filed: Jan. 24, 2020

(65) Prior Publication Data

US 2020/0237551 A1 Jul. 30, 2020

Related U.S. Application Data

(60) Provisional application No. 62/796,737, filed on Jan. 25, 2019.

(51) Int. Cl.
*A61F 5/56* (2006.01)
*A61N 1/05* (2006.01)
*A61N 1/36* (2006.01)

(52) U.S. Cl.
CPC ............ *A61F 5/566* (2013.01); *A61N 1/0548* (2013.01); *A61F 2005/563* (2013.01)

(58) Field of Classification Search
CPC ....... A61F 5/56–566; A61C 7/00; A61C 7/08; A61C 7/36; A61C 7/06; A61C 7/10; A63B 71/08–085; A63B 2071/086–088; A61N 1/00; A61N 1/02; A61N 1/04; A61N 1/05; A61N 1/0526; A61N 1/0548
See application file for complete search history.

(56) References Cited

U.S. PATENT DOCUMENTS

| | | | | |
|---|---|---|---|---|
| 4,671,767 A | * | 6/1987 | Blechman | A61C 7/006 433/18 |
| 5,871,350 A | * | 2/1999 | Clark | A61C 7/00 433/18 |
| 9,180,034 B1 | * | 11/2015 | Kapil | A63B 21/0552 |
| 2008/0041396 A1 | | 2/2008 | Lucker | |
| 2008/0199824 A1 | | 8/2008 | Hargadon | |
| 2011/0152966 A1 | | 6/2011 | Bolea | |
| 2011/0259345 A1 | * | 10/2011 | Cullen | A61F 5/566 433/214 |

(Continued)

FOREIGN PATENT DOCUMENTS

WO 2009140720 A1 11/2009

OTHER PUBLICATIONS

International Search Report for PCT/US20/15115, dated Jun. 2, 2020.

*Primary Examiner* — Michelle J Lee
(74) *Attorney, Agent, or Firm* — Novel IP

(57) ABSTRACT

Devices for treating obstructive sleep apnea include appliances for securing to one or more teeth of a patient and connected to a lingual bridge configured to change shape and apply pressure to a patient's tongue, preventing backward movement of the tongue and blockage of the patient's airway. The lingual bridge is composed of a shape memory alloy to allow the bridge to change shape once deployed in a patient's oral cavity and exposed to increased temperature in the patient's mouth. Pulse generators and electrodes are included to electrically stimulate the nerves and muscles of the tongue to assist in keeping the tongue from moving backward in the mouth during sleep.

22 Claims, 35 Drawing Sheets

(56) References Cited

U.S. PATENT DOCUMENTS

| | | | |
|---|---|---|---|
| 2014/0230829 A1* | 8/2014 | Rogers | A61C 7/36 |
| | | | 128/848 |
| 2017/0087360 A1 | 3/2017 | Scheiner | |
| 2018/0161195 A1 | 6/2018 | Carrillo Gonzalez | |
| 2018/0263806 A1 | 9/2018 | Toussaint | |

* cited by examiner

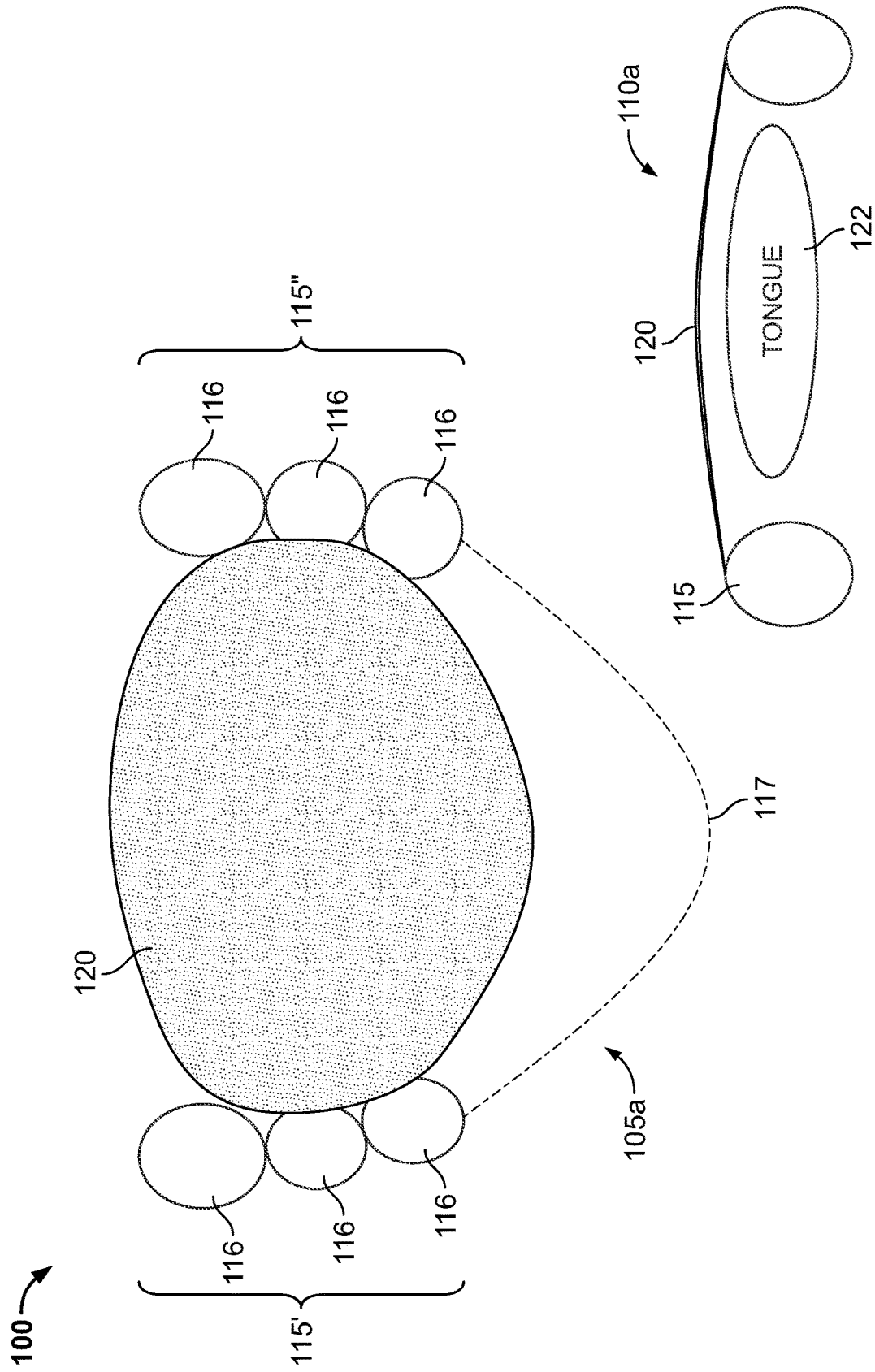

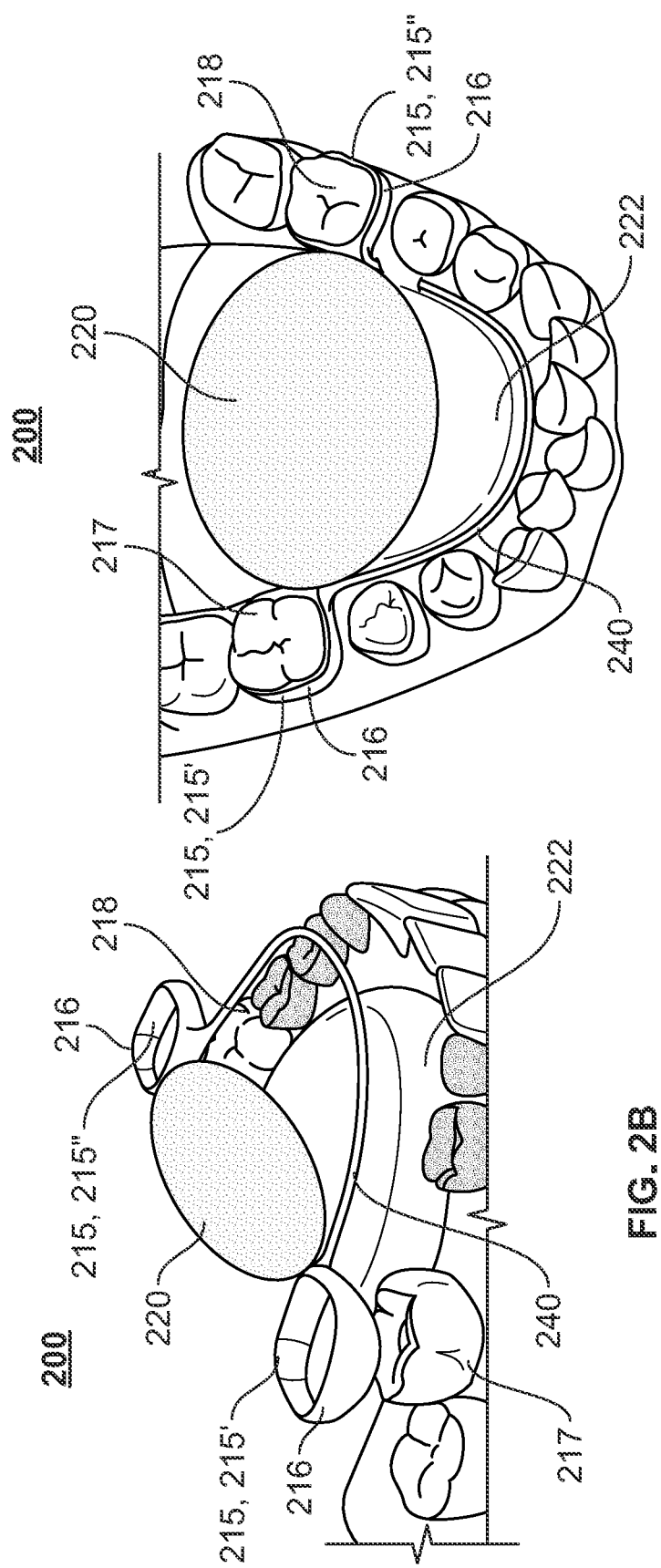

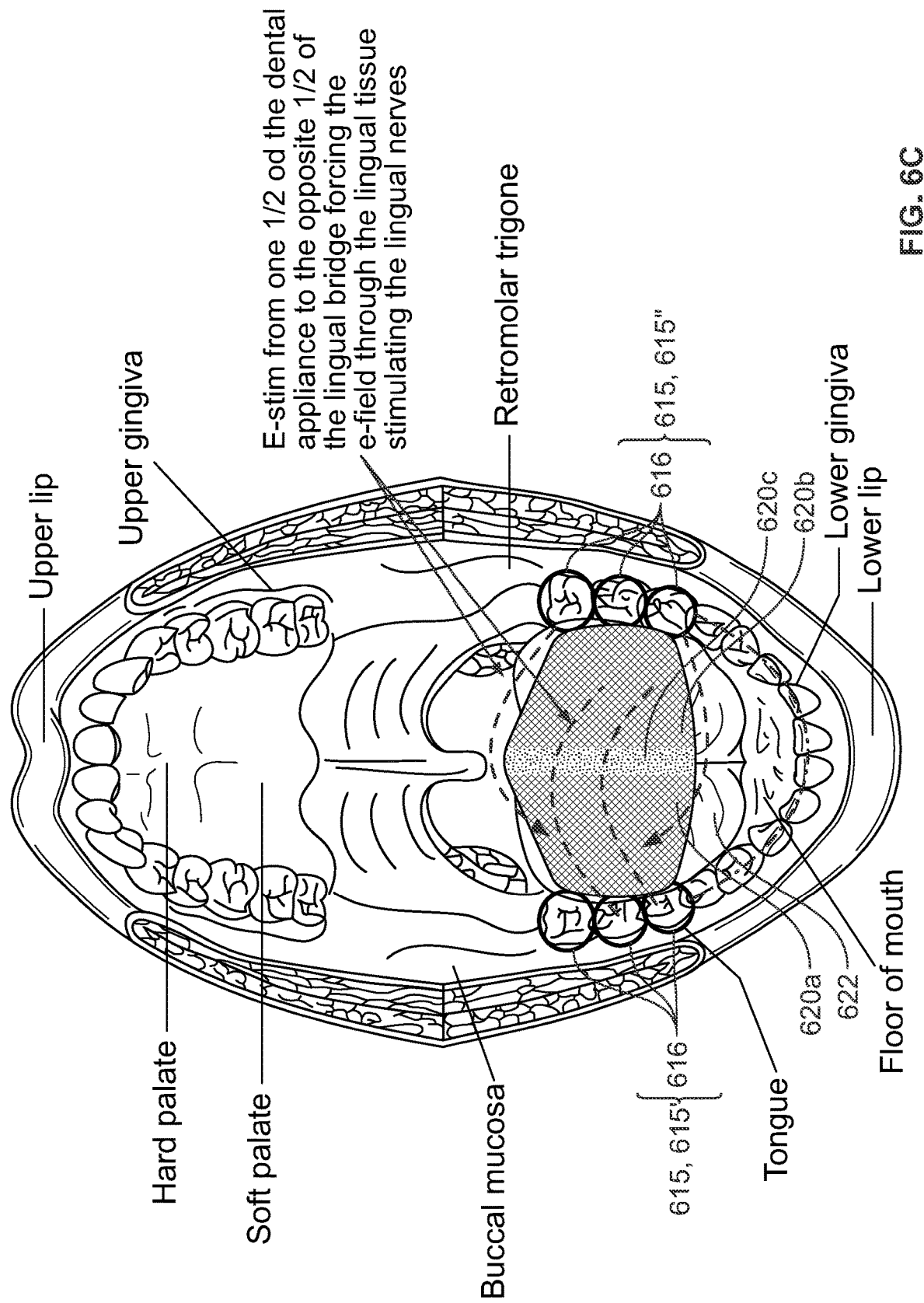

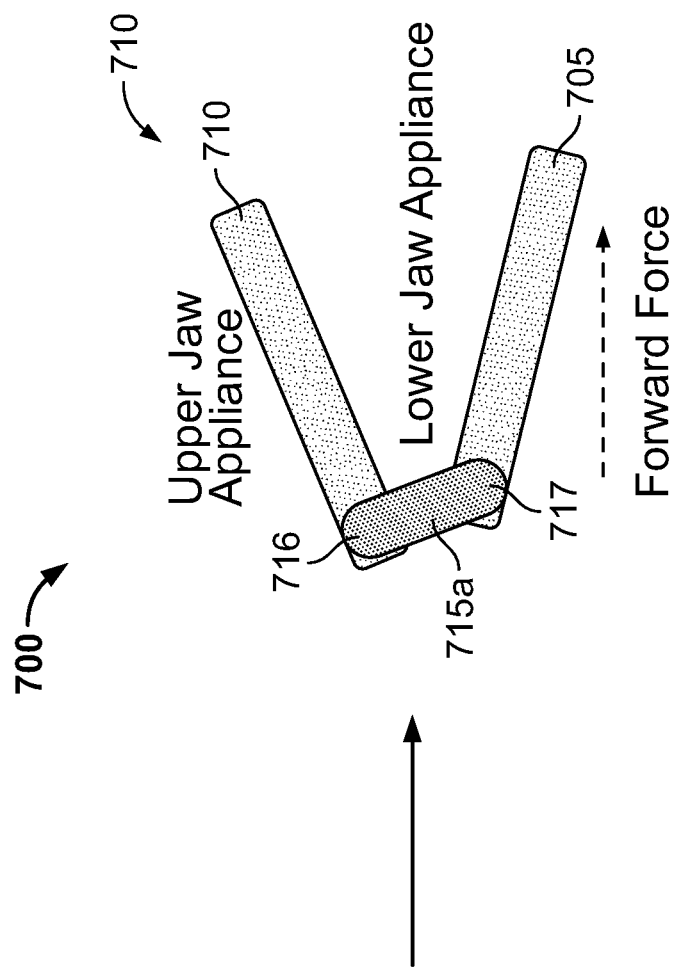
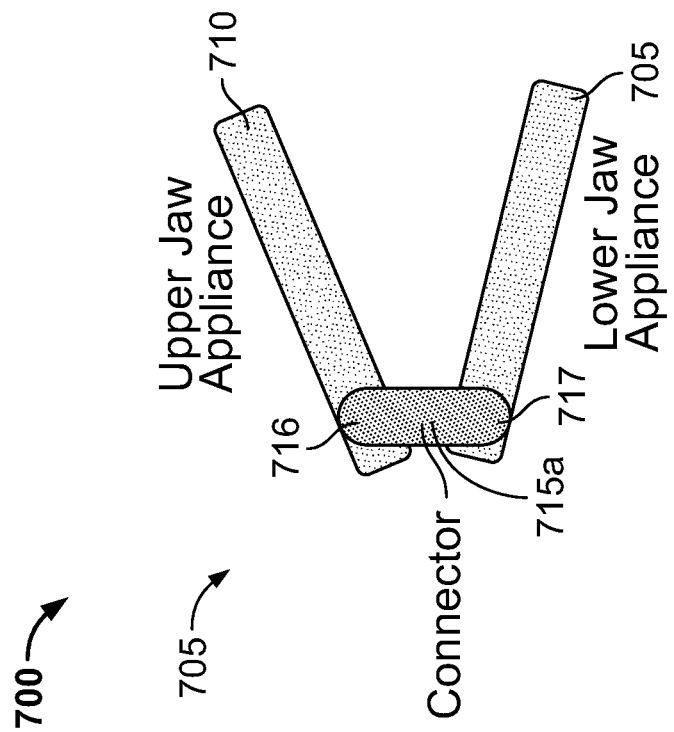
FIG. 7A

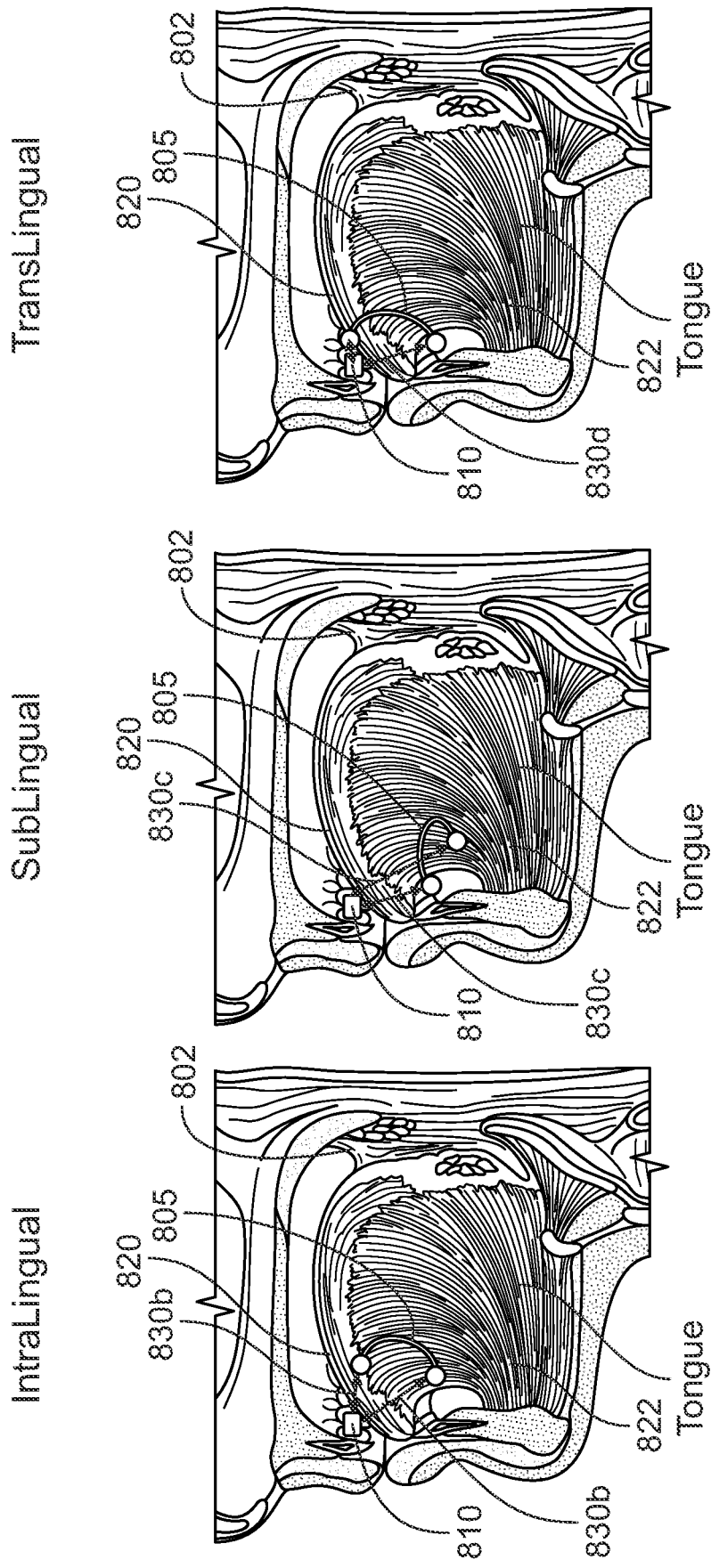

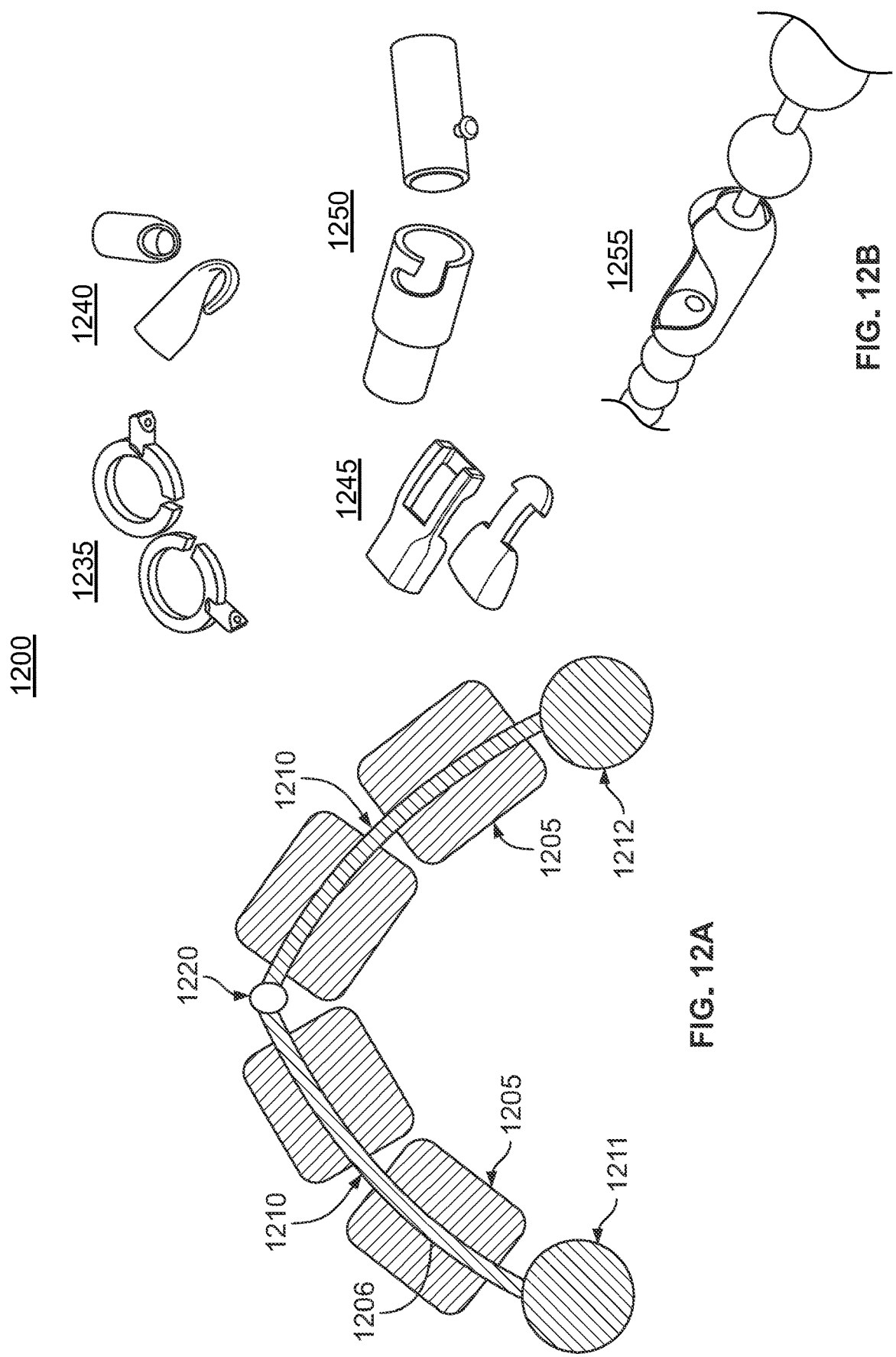

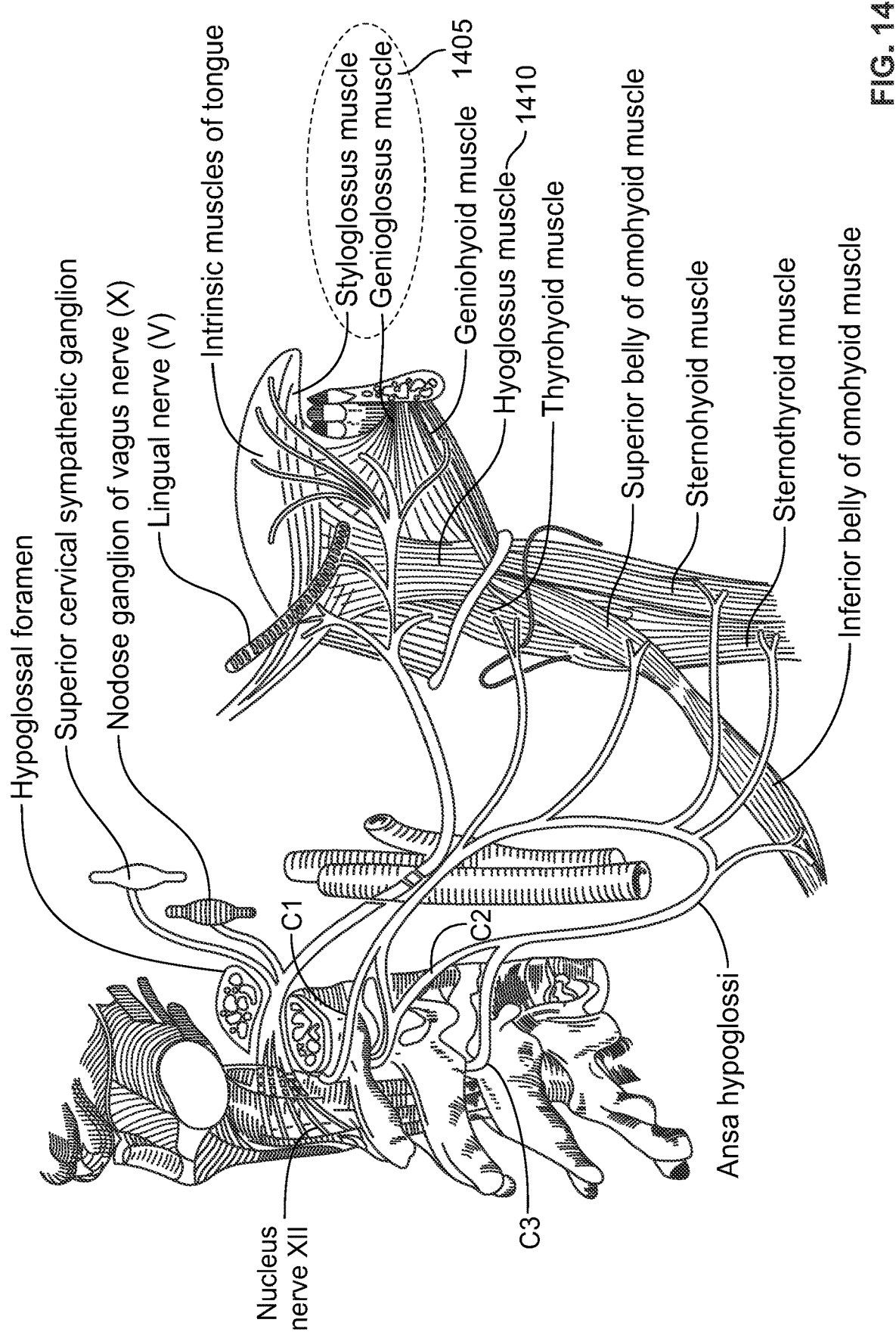

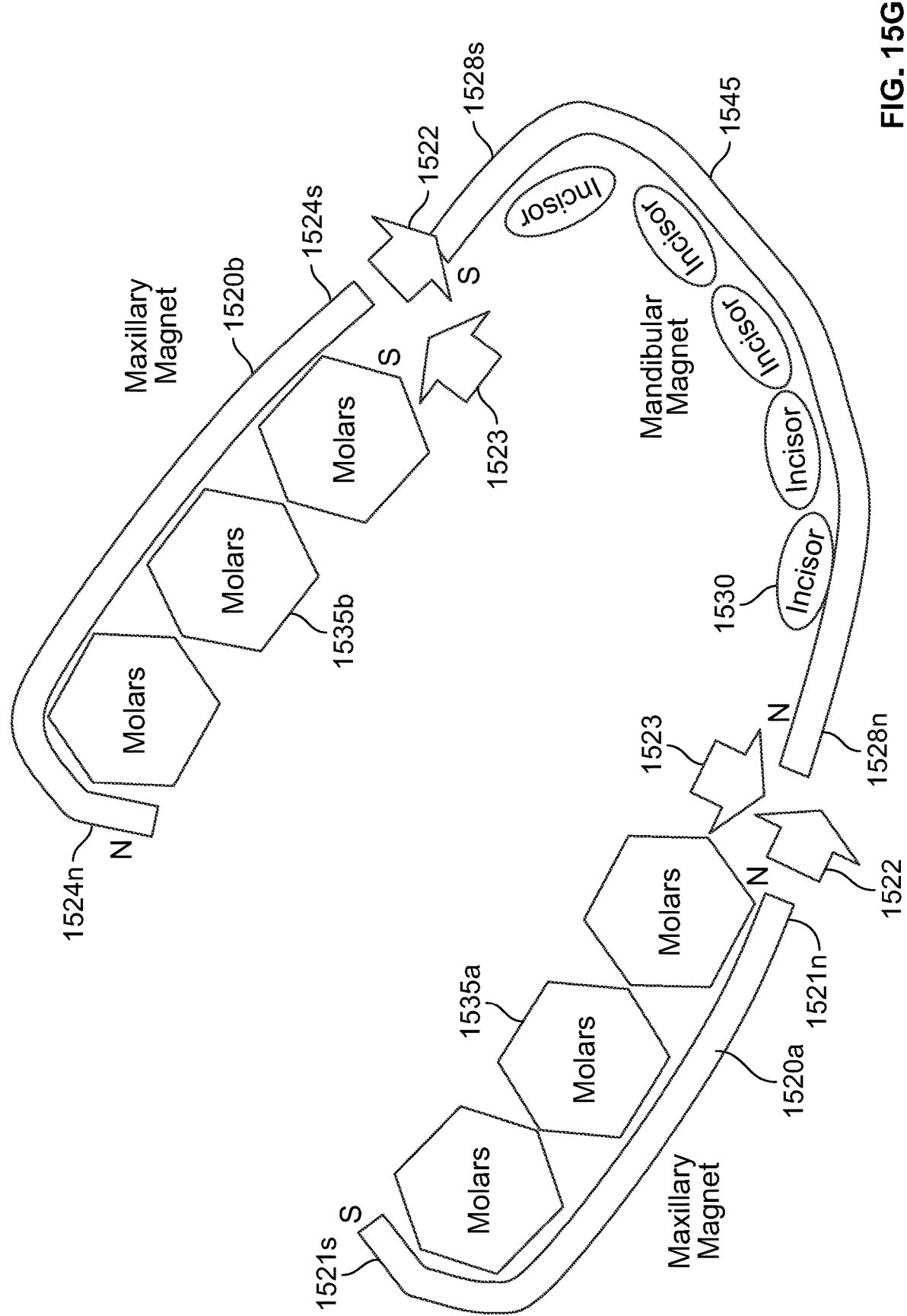

DEVICES FOR TREATING OBSTRUCTIVE SLEEP APNEA

CROSS-REFERENCE

The present specification relies on U.S. Patent Provisional Application No. 62/796,737, entitled "Devices for Treating Obstructive Sleep Apnea", and filed on Jan. 25, 2019, for priority. The above-referenced application is herein incorporated by reference in its entirety.

FIELD

The present specification is related generally to the field of sleep disorders. More specifically, the present specification is related to devices that are dentally retained and worn at night by patients for treatment of obstructive sleep apnea.

BACKGROUND

The syndrome of obstructive sleep apnea (OSA) is a common disorder, especially in middle-aged obese males. The syndrome arises due to complete or partial obstruction of a patient's pharyngeal airway during sleep. Usually airway obstruction results from an apposition of the rear portion of the tongue or soft palate with the posterior pharyngeal wall. Consequently, OSA patients experience severe interruption of sleep due to occurrence of greater intensity of asphyxia as the disease progresses. OSA, if not treated, results in reduced quality of life and increased risk of medical conditions such as hypertension, stroke, morning headaches and heart disease.

A standard treatment for OSA is continuous positive airway pressure (CPAP). While CPAP is non-invasive it is not well tolerated by patients. Patient compliance for CPAP is often lacking. Also, CPAP involves cumbersome physical equipment rendering this solution to be satisfactory only for in-hospital management of patients, hence being practical for severely affected patients. Surgical treatment options for OSA are also available. However, these tend to be generally invasive, irreversible, and have poor and/or inconsistent efficacy.

Accordingly, there is a need for devices that treat OSA without being invasive and are also well tolerated by a patient. There is also a need for devices that directly engage the patient's tongue and maintain the patient's tongue and/or mandible in an anterior, protruded position to prevent obstruction of the pharyngeal airway during sleeping.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a device for treating obstructive sleep apnea in a patient, comprising: a lower jaw appliance configured to engage the patient's mandibular dental arcade; an upper jaw appliance configured to engage the patient's maxillary dental arcade; and a first connector comprising a first member and a second member, wherein the first member and second member are configured to move relative to each other to thereby modulate a length of the first connector, wherein the first member is configured to be attached to at least one of the lower jaw appliance or upper jaw appliance, wherein the second member is configured to be attached to at least one of the lower jaw appliance or upper jaw appliance and wherein the first member and second member are not both attached to a same one of the lower jaw appliance or the upper jaw appliance.

Optionally, the device further comprises a second connector comprising a third member and a fourth member, wherein the third member and fourth member are configured to move relative to each other to thereby modulate a length of the second connector, wherein the third member is configured to be attached to at least one of the lower jaw appliance or upper jaw appliance, wherein the fourth member is configured to be attached to at least one of the lower jaw appliance or upper jaw appliance and wherein the third member and fourth member are not both attached to a same one of the lower jaw appliance or the upper jaw appliance. The first connector may be positioned on a left buccal surface of the patient's dental arcades. The second connector may be positioned on a right buccal surface of the patient's dental arcades. The first member may be a partially hollow arm configured to slidably receive the second member and the third member may be a partially hollow arm configured to slidably receive the fourth member. The second member may be configured to slide into, and out of, the first member in response to an amount of movement of the patient's mandibular dental arcade relative to an amount of movement of the patient's maxillary dental arcade and the fourth member may be configured to slide into, and out of, the third member in response to an amount of movement of the patient's mandibular dental arcade relative to an amount of movement of the patient's maxillary dental arcade. The first member may be configured to move in a telescoping manner relative to the second member and the third member may be configured to move in a telescoping manner relative to the fourth member.

Optionally, a first magnet is positioned proximate a first end of the first connector and inside the first member, and a second magnet is positioned proximate a second end of the first connector, opposing the first end, and inside the second member. The first magnet and second magnet may be oriented such that like polarities face each other and thereby generate a repulsive force configured to push the first end away from the second end. Optionally, the device further comprises a third magnet positioned between the first magnet and the second magnet, wherein the first magnet and third magnet are oriented such that like polarities face each other and thereby generate a repulsive force configured to push the first magnet and third magnet away from each other and the second magnet and third magnet are oriented such that like polarities face each other and thereby generate a repulsive force configured to push the second magnet and third magnet away from each other. Optionally, The device further comprises a second connector comprising a third member and a fourth member, wherein the third member is configured to at least partially cover the fourth member, wherein the third member and fourth member are configured to move relative to each other to thereby modulate a length of the second connector, wherein the third member is configured to be attached to at least one of the lower jaw appliance or upper jaw appliance, wherein the fourth member is configured to be attached to at least one of the lower jaw appliance or upper jaw appliance, wherein the third member and fourth member are not both attached to a same one of the lower jaw appliance or the upper jaw appliance, wherein a fourth magnet is positioned proximate a first end of the second connector and inside the third member, and wherein a fifth magnet is positioned proximate a second end of the second connector, opposing the first end, and inside the fourth member. The fourth magnet and fifth magnet may be oriented such that like polarities face each other and thereby generate a repulsive force configured to push the first end of the second connector away from the second end of the second connector. Optionally, the device further comprises a sixth magnet positioned between the fourth magnet and the fifth magnet, wherein the fourth magnet and sixth magnet are oriented such that like polarities face each other and thereby generate a repulsive force configured to push the fourth magnet and sixth magnet away from each other and wherein the fifth magnet and sixth magnet are oriented such that like polarities face each other and thereby generate a repulsive force configured to push the fifth magnet and sixth magnet away from each other.

Optionally, the device further comprises at least one elongated portion of a shape memory alloy, wherein the at least one elongated portion of the shape memory alloy is positioned inside the first connector and within the outer and inner arms and wherein the at least one elongated portion of the shape memory alloy is configured to lengthen after being placed in the patient's oral cavity and to cause the patient's lower jaw to move relative to the patient's upper jaw.

Optionally, the first member and second member are physically coupled by a sliding joint. Optionally, the sliding joint comprises a substantially U-shaped groove configured to enable the first member and the second member to be disconnected and connected.

Optionally, the device further comprises a lingual bridge coupled to the lower jaw appliance and configured to lie over, and apply pressure to, the patient's tongue, wherein such applied pressure is sufficient to prevent the patient's tongue from impeding airflow in the patient's oropharynx.

Optionally, the device further comprises at least one pulse generator and at least one electrode, wherein the at least one pulse generator and at least one electrode are electrically coupled and physically coupled to the lower jaw appliance. Optionally, the at least one pulse generator is configured to drive the at least one electrode to apply stimulation to at least one of the patient's genioglossus, the patient's hyoglossus muscle, or to a nerve supplying the patient's genioglossus or hyoglossus muscle.

The present specification also discloses a device for treating obstructive sleep apnea in a patient, comprising: a lower jaw appliance configured to engage the patient's mandibular dental arcade; an upper jaw appliance configured to engage the patient's maxillary dental arcade; a first connector comprising a first member connected to the lower jaw appliance and a second member connected to the upper jaw appliance, wherein the first member and second member are configured to slidably move relative to each other to thereby modulate a length of the first connector; a first set of magnets positioned with the first connector and configured such that a first portion of the first set of magnets is oriented relative to a second portion of the first set of magnets such that like polarities face each other and generate a repulsive force configured to push opposing ends of the first connector away from each other; a second connector comprising a third member connected to the lower jaw appliance and a fourth member connected to the upper jaw appliance, wherein the third member and fourth member are configured to slidably move relative to each other to thereby modulate a length of the second connector; a second set of magnets positioned within the second connector and configured such that a first portion of the second set of magnets is oriented relative to a second portion of the second set of magnets such that like polarities face each other and generate a repulsive force configured to push opposing ends of the second connector away from each other.

The first connector may be positioned on a left buccal surface of the patient's dental arcades. The second connector may be positioned on a right buccal surface of the patient's dental arcades.

The first member may be a partially hollow arm configured to slidably receive the second member and the third member may be a partially hollow arm configured to slidably receive the fourth member.

The second member may be a partially hollow arm configured to slidably receive the first member and the fourth member may be a partially hollow arm configured to slidably receive the third member.

The second member may be configured to slide into, and out of, the first member in response to an amount of movement of the patient's mandibular dental arcade relative to an amount of movement of the patient's maxillary dental arcade and the fourth member may be configured to slide into, and out of, the third member in response to an amount of movement of the patient's mandibular dental arcade relative to an amount of movement of the patient's maxillary dental arcade.

The first member may be configured to slide into, and out of, the second member in response to an amount of movement of the patient's mandibular dental arcade relative to an amount of movement of the patient's maxillary dental arcade and the third member may be configured to slide into, and out of, the fourth member in response to an amount of movement of the patient's mandibular dental arcade relative to an amount of movement of the patient's maxillary dental arcade.

Optionally, the device further comprises: a first element configured as a lingual implant for positioning in the patient's tongue; a second element configured as a dental implant; and a third element configured as an upper jaw dental appliance to engage the patient's maxillary dental arcade and to support said second element, wherein said first and second elements work together through magnetic forces to move the patient's tongue.

Optionally, said first element is positioned as an intra-lingual implant in the patient's tongue proximal the anterior portion while said second element is positioned at an anterior end of said third element.

Optionally, said first element is positioned as a sub-lingual implant in the patient's tongue proximal the anterior portion while said second element is positioned at an anterior end of said third element.

Optionally, said first element is positioned as a trans-lingual implant in the patient's tongue proximal the anterior portion while said second element is positioned at an anterior end of said third element.

Optionally, said first element is a curved wire with plugs at first and second ends of the wire.

Optionally, said first element comprises a plurality of atraumatic ferromagnetic elements connected by a plurality of articulating connectors.

Optionally, said second element comprises a plurality of rare-earth magnetic elements connected by a plurality of articulating connectors, each of said plurality of magnetic elements having sockets and each of said plurality of articulating connectors having connector balls at its ends, wherein said connector balls fit into said sockets to form ball and socket joints. Optionally, the device has first and second end connectors with connector balls to enable additional magnetic elements to be connected in order to modify the magnetic strength of said second element.

Optionally, said second element comprises a plurality of magnetic elements strung over a wire. Optionally, an articulating connector is incorporated at a position on the wire.

The present specification also discloses a device for treating obstructive sleep apnea in a patient, comprising: a dental appliance having a first portion with at least one engagement mechanism to reversibly engage at least one tooth at the left on the patient's mandibular dental arcade and a second portion with at least one engagement mechanism to reversibly engage at least one tooth at the right on the patient's mandibular dental arcade; and a lingual bridge coupled to the dental appliance so as to lie between the first and second portions and over the patient's tongue, wherein the lingual bridge applies therapeutic pressure on the patient's tongue, and wherein such therapeutic pressure prevents the patients tongue from impeding the airflow in a patients oropharynx.

Optionally, the lingual bridge comprises a first shape and a second shape, wherein, in the first shape, the lingual bridge does not apply a therapeutic pressure on the patient's tongue and, in the second shape, the lingual bridge does apply therapeutic pressure created by a change from the first shape to the second shape which is caused by a change in the temperature of the lingual bridge.

Optionally, each of the first and second portions has first, second and third hoops to respectively grip onto corresponding mandibular first, second and third molars.

Optionally, said first shape is characterized by a first width and a first height while the second shape is characterized by a second width and a second, and the second width is greater than the first width while the second height is lesser than the first height.

Optionally, the lingual bridge is characterized by an increase of up to 500% from the first width to the second width and a decrease of up to 400% from the first height to the second height.

Optionally, the lingual bridge is a mesh of shape memory alloy.

Optionally, each of the first and second portions has a hoop to grip onto one of mandibular first, second or third molars at the respective left and right of the patient's dental arcade, and wherein the dental appliance further includes a frame that approximately abuts and runs along a lingual surfaces of the patient's mandibular dental arcade while connecting the first and second portions. Optionally, the frame has a plurality of transverse bars towards positioned towards anterior portion of the dental appliance.

Optionally, a first pulse generator and associated plurality of electrodes are positioned in the first portion and a second pulse generator and associated plurality of electrodes are positioned in the second portion. Optionally, the first and second pulse generators drive the associated plurality of electrodes to apply therapeutic stimulation to one of a genioglossus or hyoglossus muscle or to a nerve supplying a genioglossus or hyoglossus muscle. Optionally, the lingual bridge has first and second lingual portions with a third lingual portion positioned between the first and second lingual portions, said first and second lingual portions being electrically conductive while the third lingual portion being electrically non-conductive. Optionally, stimulation from said plurality of electrodes in the first portion flows to the second lingual portion thereby causing the stimulation to be forced through the patient's tongue in a first direction, and stimulation from said plurality of electrodes in the second portion flows to the first lingual portion thereby causing the stimulation to be forced through the patient's tongue in a second direction, said first and second directions being substantially opposite to each other.

The present specification also discloses a device for treating obstructive sleep apnea in a patient, comprising: a dental appliance having first and second portions that together form a substantially U-shaped frame and engage a plurality of patient's teeth on the mandibular dental arch; and a lingual bridge coupled to the dental appliance so as to lie between the first and second portions and over the patient's tongue, said lingual bridge having a first shape and a second shape, wherein in said first shape the lingual bridge does not apply therapeutic pressure on the patient's tongue while in said second shape the lingual bridge applies therapeutic pressure on the patient's tongue, and wherein a change from the first shape to the second shape is caused by a change in temperature in the patient's mouth while sleeping.

Optionally, a first pulse generator and associated plurality of electrodes are positioned in the first portion and a second pulse generator and associated plurality of electrodes are positioned in the second portion. Optionally, the first and second pulse generators drive the associated plurality of electrodes to apply therapeutic stimulation to one of a genioglossus or hyoglossus muscle or to a nerve supplying a genioglossus or hyoglossus muscle.

Optionally, said first shape is characterized by a first width and a first height while the second shape is characterized by a second width and a second, and the second width is greater than the first width while the second height is lesser than the first height.

Optionally, the lingual bridge is characterized by an increase of up to 500% from the first width to the second width and a decrease of up to 400% from the first height to the second height.

Optionally, a first pulse generator and associated plurality of electrodes are positioned in the first portion and a second pulse generator and associated plurality of electrodes are positioned in the second portion. Optionally, the first and second pulse generators drive the associated plurality of electrodes to apply therapeutic stimulation to one of a genioglossus or hyoglossus muscle or to a nerve supplying a genioglossus or hyoglossus muscle. Optionally, the lingual bridge has first and second lingual portions with a third lingual portion positioned between the first and second lingual portions, said first and second lingual portions being electrically conductive while the third lingual portion being electrically non-conductive. Optionally, stimulation from said plurality of electrodes in the first portion flows to the second lingual portion thereby causing the stimulation to be forced through the patient's tongue in a first direction, and stimulation from said plurality of electrodes in the second portion flows to the first lingual portion thereby causing the stimulation to be forced through the patient's tongue in a second direction, said first and second directions being substantially opposite to each other.

The present specification also discloses a device for treating obstructive sleep apnea in a patient, comprising: a lower jaw appliance and an upper jaw appliance, wherein said lower jaw appliance is configured to engage the patient's mandibular dental arcade while said upper jaw appliance is configured to engage the patient's maxillary dental arcade; and a first connector and a second connector, each of said first and second connectors having an upper end coupled to the upper jaw appliance and a lower end coupled to the lower jaw appliance, wherein said first and second connectors are respectively positioned at left and right towards the buccal surface of the patient's dental arcades.

Optionally, said first and second connectors are made of shape memory alloy which expand in the patient's oral cavity to apply forward force on the patient's lower jaw.

Optionally, said first and second connectors are made of shape memory alloy which contract in the patient's oral cavity thereby pulling the patient's lower jaw forward.

Optionally, said first and second connectors are motorized components with pistons that apply a forward pressure on the lower jaw appliance.

Optionally, each of said first and second connectors comprise telescoping outer and inner arms having magnetic components with magnetic repulsive forces that apply a forward pressure on the lower jaw appliance.

The present specification also discloses a device for treating obstructive sleep apnea in a patient, comprising: a first element configured as a lingual implant for positioning in the patient's tongue; a second element configured as a dental implant; and a third element configured as an upper jaw dental appliance to engage the patient's maxillary dental arcade and to support said second element, wherein said first and second elements work together through magnetic forces to move the patient's tongue.

Optionally, said first element is positioned as an intra-lingual implant in the patient's tongue proximal the anterior portion while said second element is positioned at an anterior end of said third element.

Optionally, said first element is positioned as a sub-lingual implant in the patient's tongue proximal the anterior portion while said second element is positioned at an anterior end of said third element.

Optionally, said first element is positioned as a trans-lingual implant in the patient's tongue proximal the anterior portion while said second element is positioned at an anterior end of said third element.

Optionally, said first element is a curved wire with plugs at first and second ends of the wire.

Optionally, said first element comprises a plurality of atraumatic ferromagnetic elements connected by a plurality of articulating connectors.

Optionally, said second element comprises a plurality of rare-earth magnetic elements connected by a plurality of articulating connectors, each of said plurality of magnetic elements having sockets and each of said plurality of articulating connectors having connector balls at its ends, and wherein said connector balls fit into said sockets to form ball and socket joints. Optionally, the device has first and second end connectors with connector balls to enable additional magnetic elements to be connected in order to modify the magnetic strength of said second element.

Optionally, said second element comprises a plurality of magnetic elements strung over a wire. Optionally, an articulating connector is incorporated at a position on the wire.

In some embodiments that use magnets to treat sleep apnea, magnetic field shields are applied to direct the magnetic field preferably into the patient's oral cavity and minimize the spread of magnetic field outside the patient's oral cavity. The magnetic shielding could be effectuated by using layers of Mu-metal coating. Other materials for magnetic shielding include Co-NETIC®, supermalloy, supermumetal, NILOMAG®, sanbold, molybdenum permalloy, Sendust, M-1040, Hipernom®, HyMu 80 and Amumetal. Pyrolytic graphite can be used for its magnetic field exclusion properties.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 1B illustrates top planar and side cross-sectional views of the device of FIG. 1A in a post-deployment configuration, in accordance with some embodiments of the present specification;

FIG. 2B is a first illustration of positioning of the device of FIG. 2A in a patient's oral cavity, in accordance with some embodiments of the present specification;

FIG. 2C is a second illustration of positioning of the device of FIG. 2A in a patient's oral cavity, in accordance with some embodiments of the present specification;

FIG. 6C illustrates positioning of the device of FIG. 6A in a patient's oral cavity with flow of electrical field from one half of the oral cavity to the other half of the oral cavity, in accordance with some embodiments of the present specification;

FIG. 7A shows first and second side views of a device for treating obstructive sleep apnea, in accordance with some embodiments of the present specification;

FIG. 8B illustrates an intra-lingual positioning of a lingual implant of the device of FIG. 8A, in accordance with some embodiments of the present specification;

FIG. 8C illustrates a sub-lingual positioning of a lingual implant of the device of FIG. 8A, in accordance with some embodiments of the present specification;

FIG. 8D illustrates a trans-lingual positioning of a lingual implant of the device of FIG. 8A, in accordance with some embodiments of the present specification;

FIG. 12A illustrates a cross-sectional view of a dental implant, in accordance with some embodiments of the present specification;

FIG. 12B illustrates first, second, third, fourth and fifth configurations of an articulating connector, in accordance with some embodiments of the present specification;

FIG. 14 shows genioglossus and hyoglossus muscles of a tongue;

FIG. 15G illustrates a fourth positional configuration of mandibular and maxillary magnets within lower and upper jaw appliances, in accordance with some embodiments of the present specification.

DETAILED DESCRIPTION

The present specification is directed towards multiple embodiments for methods and devices that directly engage a patient's tongue pulling it forward or preventing it from falling backward into the oropharyngeal space hence preventing it from obstructing the oropharyngeal airway. The present specification is also directed towards multiple embodiments for methods and devices that directly engage differing portions of a patient's maxillary and/or mandibular jaw and associated teeth for adjusting the relative positions of the patient's upper and lower jaw with the therapeutic intent of opening a patients airway or preventing the patients airway from closing during sleep.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

Figure 1A:
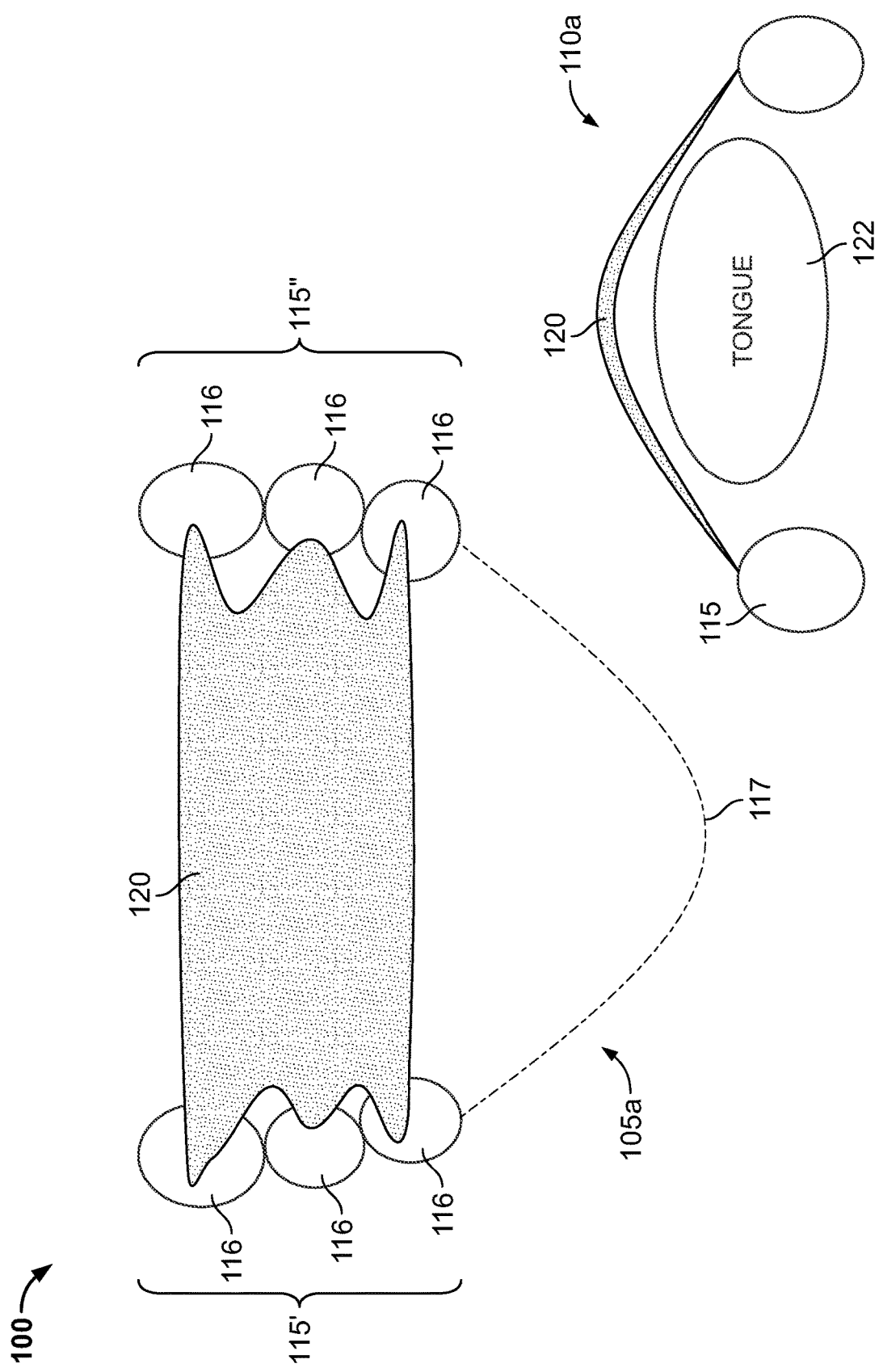
FIG. 1A illustrates top planar and front-to-back cross-sectional views of a device in a pre-deployment configuration, in accordance with some embodiments of the present specification.

FIG. 1A is an embodiment of a device 100 which prevents a tongue from falling backwards into an oropharyngeal airway and illustrates top planar and front-to-back cross-sectional views 105a, 110a respectively, of the device 100, in a pre-deployment configuration while FIG. 1B illustrates top planar and front-to-back cross-sectional views 105b, 110b respectively, of the device 100 in a post-deployment configuration, for treating obstructive sleep apnea, in accordance with some embodiments of the present specification. The device 100 comprises a dental appliance, component or fixture 115 and a lingual bridge 120 connected to, and extending between, two portions of the dental appliance 115.

The dental appliance 115 is configured to engage at least two teeth of a patient's mandibular dental arcade while the lingual bridge 120 is configured to engage the tongue 122. In some embodiments, the dental appliance 115 has a first portion 115' to engage one or more teeth (or all teeth) of the right mandibular dental arcade and a second portion 115" to engage one or more teeth (or all teeth) of the left mandibular dental arcade. In embodiments, the lingual bridge 120 is coupled or attached to the dental appliance 115 so as to lie between the first and second portions 115', 115" and over the tongue 122.

In embodiments, the first portion 115' comprises at least one hoop or loop structure 116 to accommodate and thereby anchor to or engage at least one tooth of the right mandibular dental arcade. Similarly, the second portion 115" also comprises at least one hoop or loop structure 116 to accommodate and thereby anchor to or engage at least one tooth of the left mandibular dental arcade. In embodiments, the at least one hoop or loop structure 116, of each of the first and second portions 115', 115", is custom shaped and sized to girdle, hold or grip a tooth.

Figure 1C:
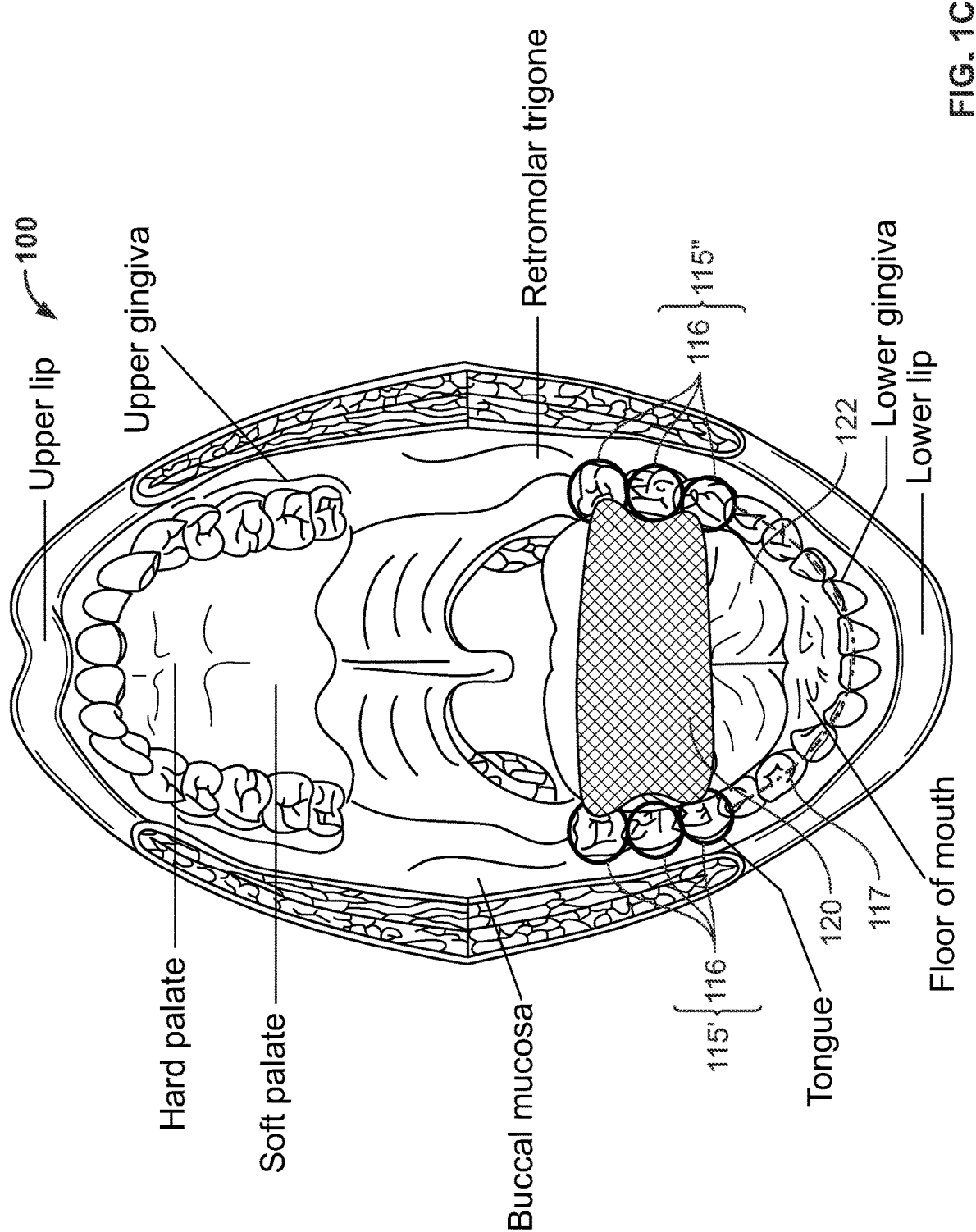
FIG. 1C shows the device of FIG. 1A being implanted in a patient's oral cavity, in accordance with some embodiments of the present specification.

In one embodiment, the first portion 115' comprises first, second and third hoop or loop structures 116 that are custom shaped and sized to girdle, hold or grip onto mandibular first, second and third molars, respectively, of the right mandibular dental arcade. The second portion 115" also comprises first, second and third hoop or loop structures 116 that are custom shaped and sized to girdle, hold or grip onto mandibular first, second and third molars, respectively, of the left mandibular dental arcade. In some embodiments, the device 100 includes an optional support member 117 connecting the first portion 115' and second portion 115". In some embodiments, the support member 117 is attached to the forward most hoop or loop structure 116 of the first portion 115' and forward most hoop or loop structure 116 of the second portion 115" and extends in an arc shape toward the front of a patient's mouth. As shown in FIG. 1C, the device 100 is implanted such that the first, second and third hoop or loop structures 116 of the first portion 115' fit onto and grip the mandibular first, second and third molars on the right while the first, second and third hoop or loop structures 116 of the second portion 115" fit onto and grip the mandibular first, second and third molars on the left. As shown, the lingual bridge 120 is positioned above the patient's tongue 122.

In various embodiments, the number of hoop or loop structures 116 may be one or more for each of the first and second portions 115', 115". In embodiments where the dental appliance 115 has one hoop or loop structure 116, for each of the first and second portions 115', 115", the structure 116 is custom shaped and sized so as to grip or hold and anchor to any one of the mandibular first, second or third molars.

Figure 1D:
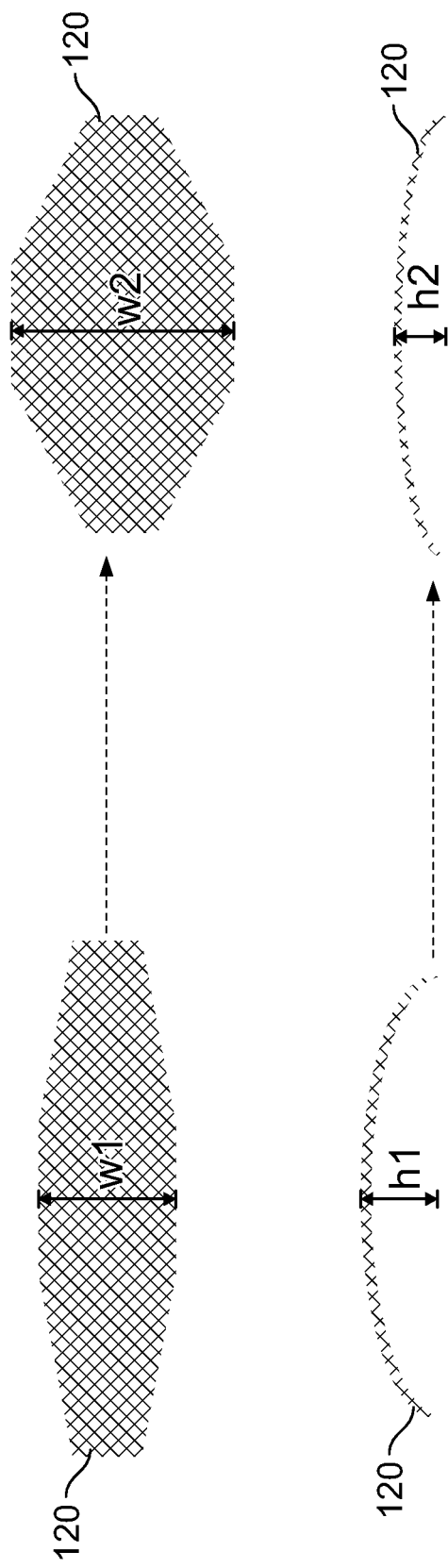
FIG. 1D illustrates modification of a lingual bridge from a first shape to a second shape, in accordance with some embodiments of the present specification.

Referring now to FIGS. 1A, 1B and 1D, in a predeployment configuration the lingual bridge 120 has a first shape characterized by a first width '$w_1$' and a first height or arch '$h_1$'. First height or arch '$h_1$' is defined as the distance from a bottom surface of the lingual bridge 120, when in a pre-deployment configuration, to a top surface of a tongue 122 of the patient. In embodiments, the first shape is substantially arched or contoured to the patient's tongue 122 and does not apply a significant or therapeutic pressure on the tongue 122. In post-deployment configuration the lingual bridge 120 has a second shape characterized by a second width '$w_2$' and a second height or arch '$h_2$'. Second height or arch '$h_2$' is defined as the distance from a bottom surface of the lingual bridge 120, when in a post-deployment configuration, to a top surface of a tongue 122 of the patient. In embodiments, the second shape is substantially flat such that the lingual bridge 120 applies a therapeutic level of pressure, such as a level of pressure in a range of 0.01 psi to 5 psi, on the tongue 122 causing the tongue 122 to move downward and/or forward, thereby preventing the tongue 122 from falling back into the oropharyngeal passage way while the patient is asleep. In embodiments, the lingual bridge 120 is a mesh made of shape memory allow such as, but not limited to, Nitinol and is optionally coated with a soft membrane of silicone, PTFE, ePTFE, or a fabric. Thus, modification of the lingual bridge 120 from the first shape to the second shape is affected by a change in temperature from a room temperature or lower to a body temperature within the patient's mouth.

As shown in FIG. 1D, in some embodiments, the lingual bridge 120 is a full Nitinol mesh that changes from the first shape (in pre-deployment stage) to the second shape (in post-deployment stage) when positioned within the patient's mouth. In embodiments, the second width '$w_2$' is greater than the first width '$w_1$' while the second height '$h_2$' is lesser than the first height '$h_1$' of the lingual bridge 120. In some embodiments, the lingual bridge 120 is characterized by an increase of up to 500% from the first width to the second width and a decrease of up to 400% from the first height to the second height. In some embodiments, the lingual bridge 120 has a narrow oval shape that increases in width as the lingual bridge 120 changes from the first shape in the pre-deployment configuration to the second shape in the post-deployment configuration. It should be appreciated that the lingual bridge could have any shape, such as rectangular, polygonal or any other freeform shape, such that it is configured to push the tongue down and/or pull the tongue forward.

Notwithstanding the above, it should be appreciated that the relative dimensions will be customized to each patient and will be based on the individual's particular tongue and oral cavity shape and size. In another embodiment, the lingual bridge 120 will be manufactured in a range of fixed or default sizes, such as 2-7 units, and a patient will first be fitted with a device having a default size closest to the patient's tongue and oral cavity shape and size. The default or fixed size device will then be modified to be customized to the patient's tongue and oral cavity shape and size.

Figure 2A:
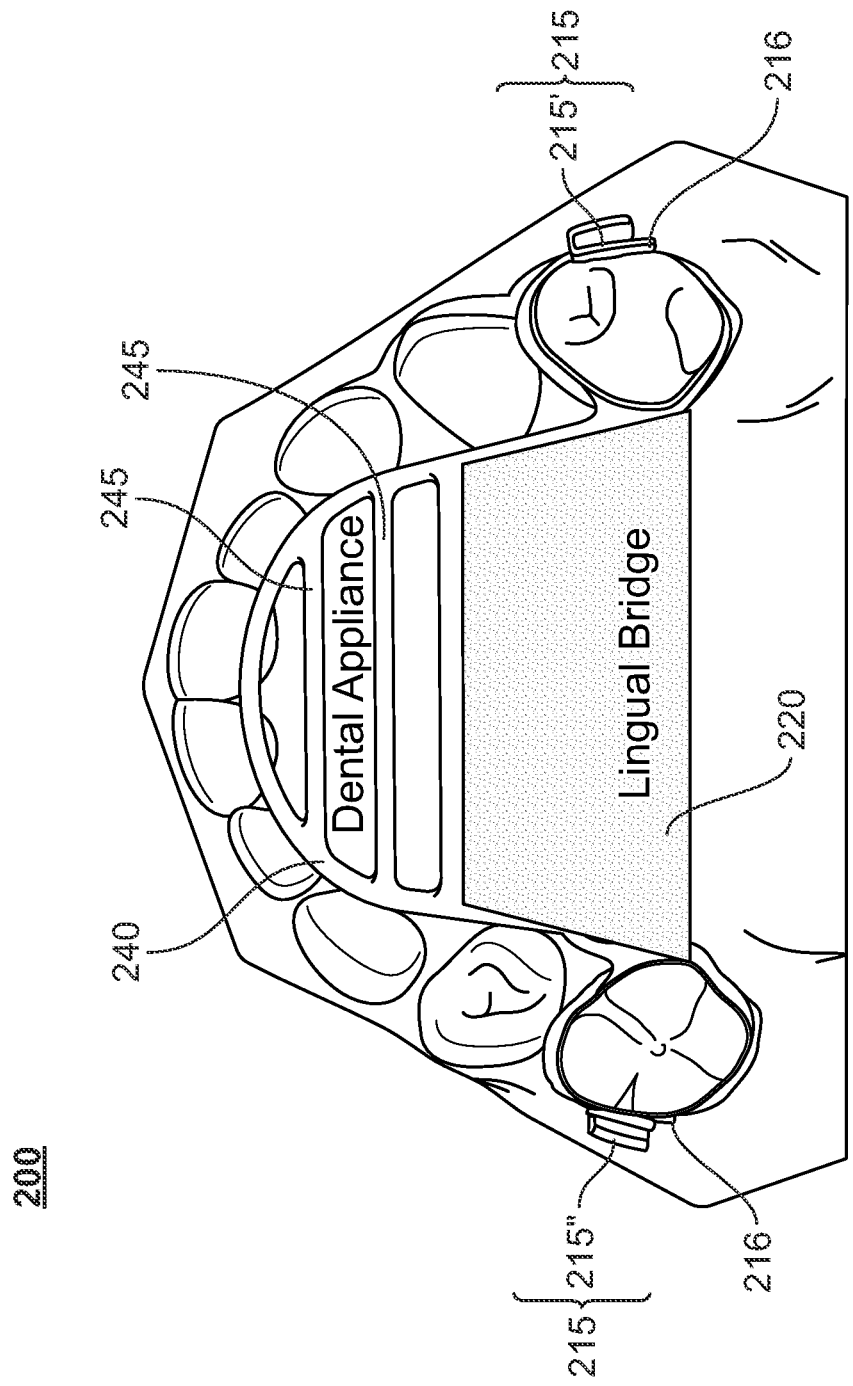
FIG. 2A shows a perspective view of a device for treating obstructive sleep apnea, in accordance with some embodiments of the present specification.

FIG. 2A shows a perspective view of a device 200 for treating obstructive sleep apnea while FIGS. 2B and 2C illustrate positioning or deployment of the device 200 in a patient's oral cavity, in accordance with some embodiments of the present specification. Referring now to FIGS. 2A, 2B and 2C, the device 200 comprises a dental appliance, component or fixture 215 and a lingual bridge 220 connected to, and extending between, two portions of the dental appliance 215. The dental appliance 215 is configured to engage the patient's teeth while the lingual bridge 220 is configured to engage the tongue 222. The dental appliance 215 has a first portion 215' to engage a tooth of the right mandibular dental arcade and a second portion 215" to engage a tooth of the left mandibular dental arcade. The lingual bridge 220 is coupled or attached to the dental appliance 215 so as to lie between the first and second portions 215', 215" and over the tongue 222.

In one embodiment, the first portion 215' comprises a single hoop or loop structure 216 that is custom shaped and sized to girdle, hold or grip any one of the mandibular molars of the right mandibular dental arcade. The second portion 215" also comprises a single hoop or loop structure 216 that is custom shaped and sized to girdle, hold or grip any one of the mandibular molars of the left mandibular dental arcade.

In an embodiment, the dental appliance 215 further includes a frame component 240 that is custom shaped and sized to approximately abut and run along the lingual surfaces of the patient's mandibular dental arcade while connecting the first and second portions 215', 215". In some embodiments, the frame component 240 is substantially U-shaped. In some embodiments, as shown in FIG. 2A, the frame component 240 has a plurality of transverse bars or grids 245 positioned towards an anterior portion of the dental appliance 215 such that the lingual bridge 220 is positioned towards a posterior portion of the dental appliance 215. The transverse bars or grids 245 are configured to provide structural stability to the bridge 220 and help hold the tongue in place, particularly while the lingual bridge 220 is shape-setting. In some embodiments the frame component 240 can run on the outer labial surface of the patient's mandibular dental arcade.

As shown in FIGS. 2B and 2C, the device 200 is implanted, inserted or positioned within the patient's oral cavity such that the hoop or loop structure 216 of the first portion 215' fits onto and grips a mandibular molar 217 on the right, the hoop or loop structure 216 of the second portion 215" fits onto and grips a mandibular molar 218 on the left, while the frame component 240 abuts the lingual surfaces of the patient's mandibular dental arcade. As shown, the lingual bridge 220 is positioned above the patient's tongue 222.

Figure 3:
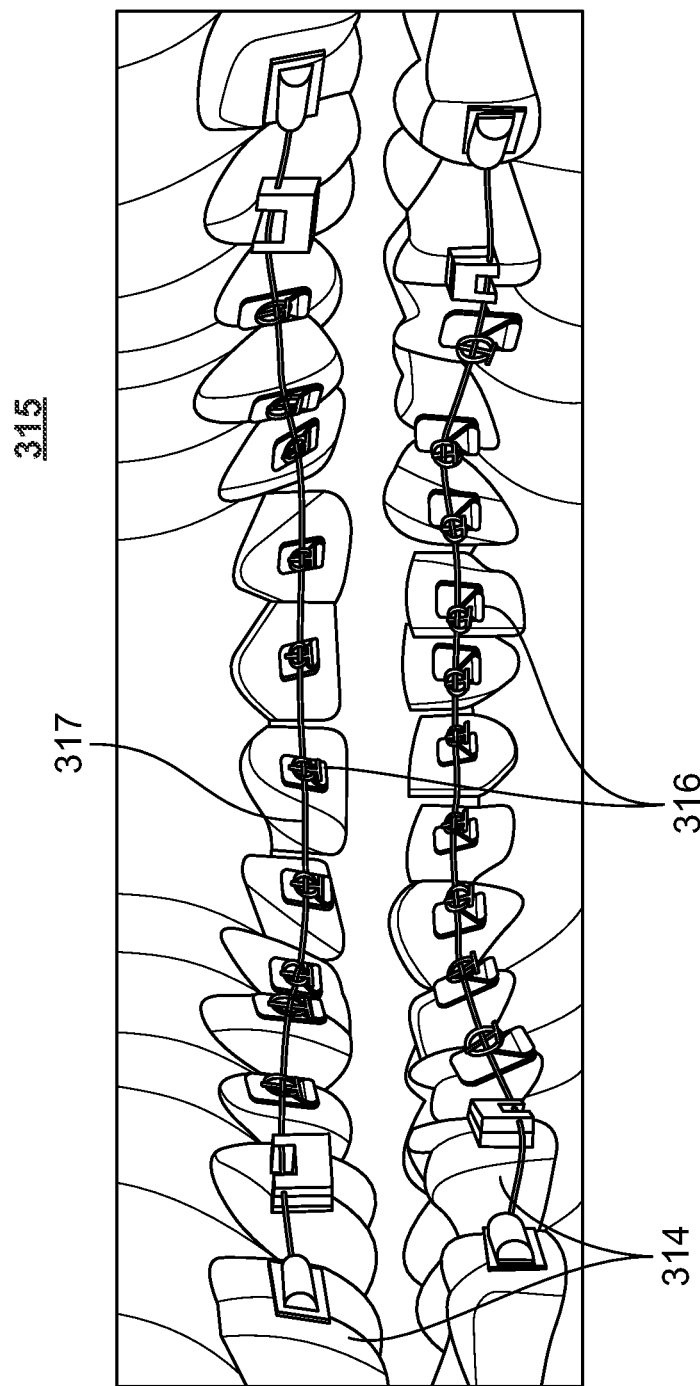
FIG. 3 shows a dental appliance, in accordance with some embodiments of the present specification.

FIG. 3 shows a dental appliance 315, in accordance with some embodiments of the present specification. The dental appliance 315 comprises a plurality of attachments 316 affixed to the lingual surfaces of a plurality of teeth 314 of a patient's mandibular and maxillary dental arcades. The plurality of attachments 316 are flexibly coupled to each other with a stainless steel, nitinol wire or a silk thread 317. A lingual bridge attaches to one or more of these wires 317 on the mandibular appliance. The plurality of attachments 316 may be permanently affixed, glued to the inner surface of the teeth 314, or be removably attached using hooks, hoops or loops structure.

Figure 4:
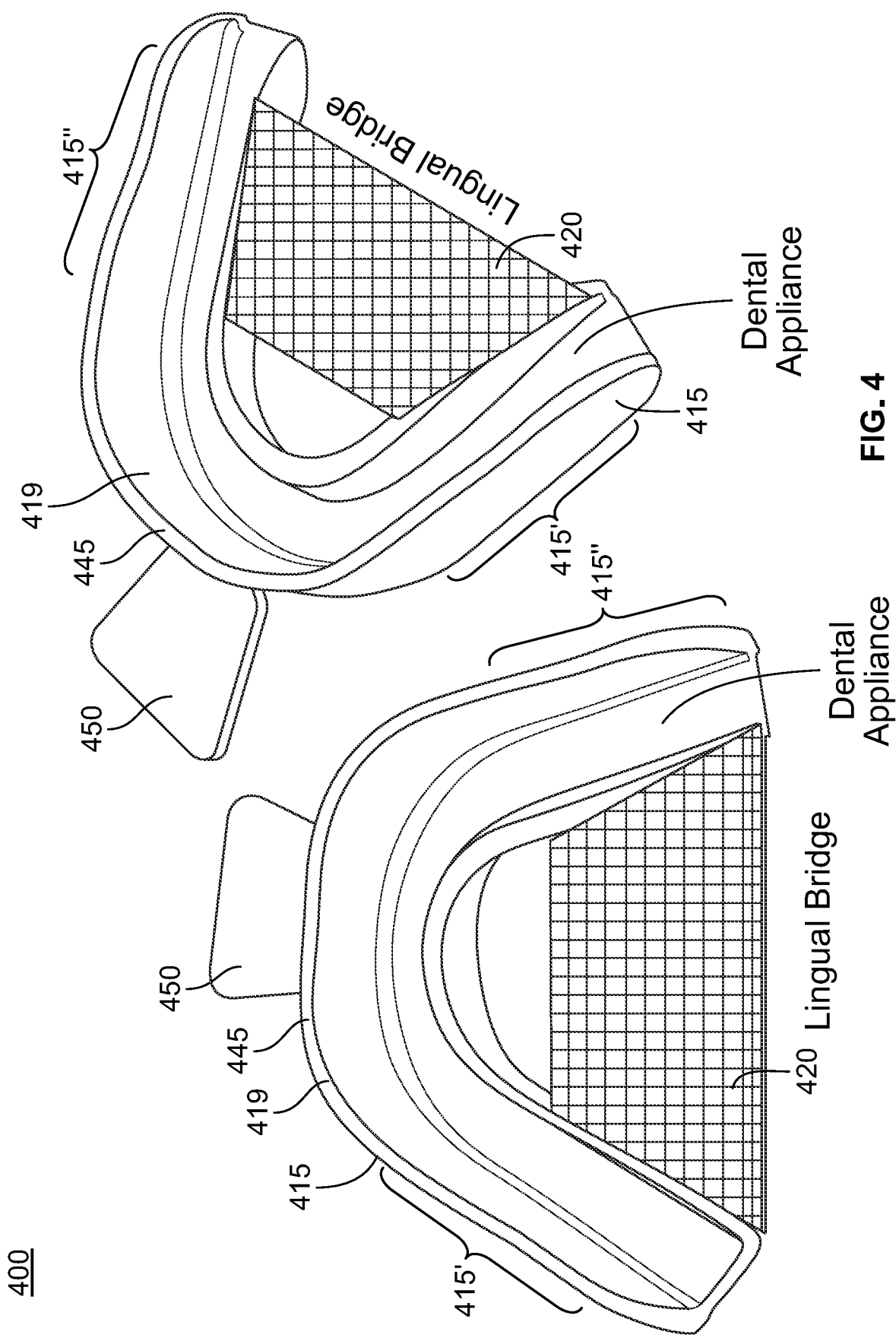
FIG. 4 shows perspective views of a device for treating obstructive sleep apnea, in accordance with some embodiments of the present specification.

FIG. 4 shows perspective views of a device 400 for treating obstructive sleep apnea, in accordance with some embodiments of the present specification. The device 400 comprises a dental appliance, component or fixture 415 and a lingual bridge 420. The dental appliance 400 is a molded component that is custom shaped and sized to fit over and engage a plurality of patient's teeth on the mandibular dental arch while the lingual bridge 420 is configured to engage the patient's tongue. The dental appliance 415 has first and second portions 415', 415" and a connecting portion 419 that together form a substantially U-shaped frame of the appliance 400 resembling a contour of the patient's mandibular dental arch. The lingual bridge 420 is coupled or attached to the dental appliance 415 so as to lie between the first and second portions 415', 415" and over the tongue. In some embodiments, the lingual bridge 420 is positioned towards a posterior portion of the dental appliance 415. In some embodiments, the first portion 415', second portion 415", and connecting portion 419 are shaped as inverted valleys with walls, such that they may be placed over the teeth of the patient's mandibular arcade. In some embodiments, the device 400 is composed of a heat sensitive material such that it may be exposed to high temperatures, such as hot water, for a period of time and then placed over the patient's teeth. Heating the device 400 makes it pliable so it may be form fitted over the patient's teeth. The device 400 is then allowed to cool in the patient's mouth, providing a custom form fit for the patient. The dental appliance 400 is held in place by the custom fit and by pressure from the upper jaw teeth onto the flat top surface of the device 400. The flat surface can be custom molded to accommodate the surface of the maxillary teeth. In one embodiment the upper surface is also custom shaped and sized to loosely fit over and engage a plurality of patient's upper teeth, allowing for the upper teeth to slide easily in and out of the appliance while opening and closing the mouth while the lower portion is a more tighter custom fit which stay in place while opening or closing the mouth. Additionally adhesive such as Fixodent® can be applied to the lower teeth portion of the appliance 400 to further fix it to the lower teeth.

In some embodiments, the dental appliance 400 also includes a handle or grip portion 450 that extends anteriorly from an anterior end 445 of the appliance 400 when the dental appliance 400 is positioned in the patient's oral cavity. The handle or grip portion 450 may be used by a patient to place, remove, and maneuver the appliance 400 with respect to the patient's mouth, teeth, and tongue.

Figure 5:
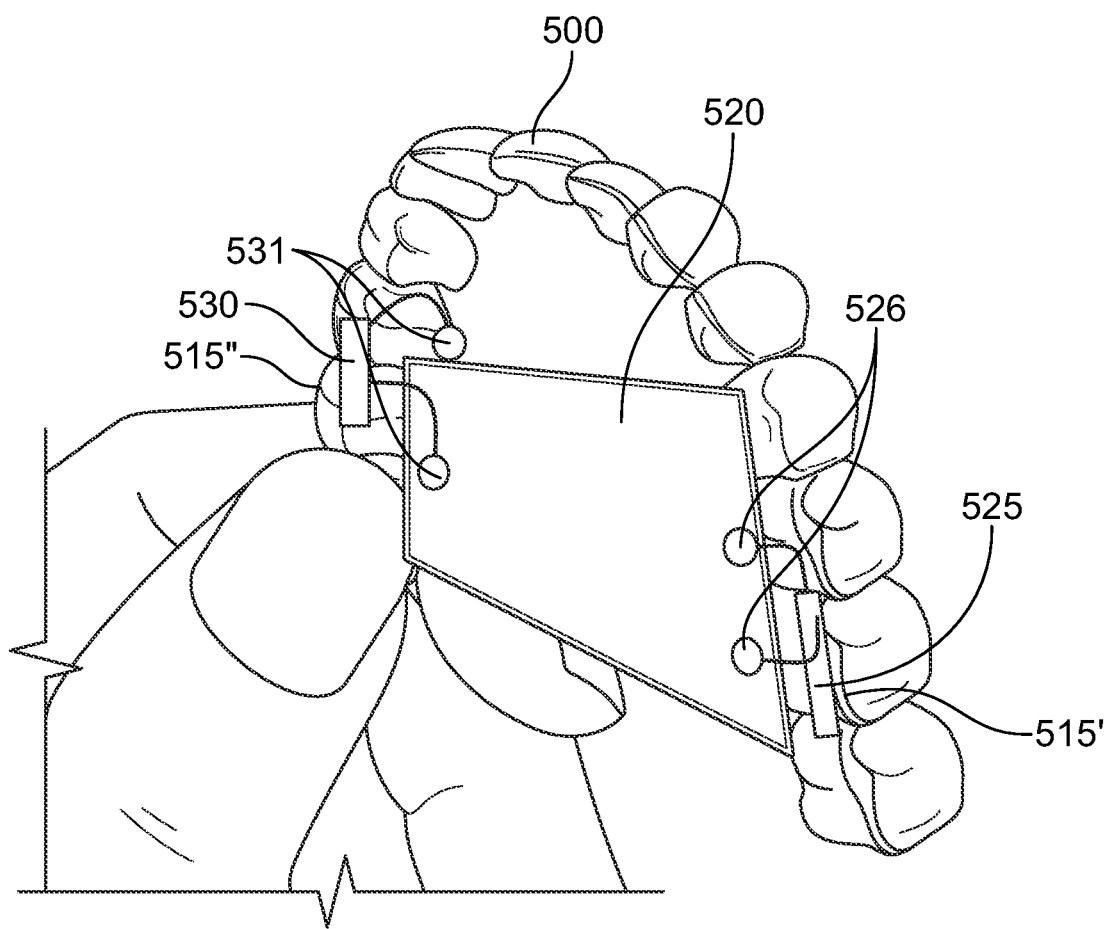
FIG. 5 shows first and second pulse generators and associated plurality of electrodes incorporated in a dental appliance, in accordance with some embodiments of the present specification.

In accordance with an aspect, a plurality of stimulating electrodes are incorporated into the dental appliance or into the lingual bridge of any of the embodiments of the present specification. In accordance with another aspect, at least one pulse generator is housed in the dental appliance of any of the embodiments of the present specification. FIG. 5 shows a first pulse generator 525 with associated stimulating electrodes 526 incorporated in a first portion 515' and a second pulse generator 530 with associated stimulating electrodes 531 incorporated in a second portion 515" of a dental appliance 500, in accordance with some embodiments of the present specification. Thus, a pulse generator and associated stimulating electrodes is positioned on each side of the lingual bridge 520. In various embodiments, the dental appliance is any one of the dental appliance 115, 215, 415 of FIGS. 1A, 2A and 4. In another embodiment there is one pulse generator with plurality of electrodes configured to drive an electrical field to the base of a patient's tongue, into a hyoglossus, styloglossus or a genioglossus muscle or to a nerve supplying a hyoglossus, styloglossus or a genioglossus muscle.

In embodiments, the stimulating electrodes 526, 531 are driven by the associated first and second pulse generators 525, 530 to apply therapeutic stimulation to one of a styloglossus, genioglossus or hyoglossus muscle or to a nerve supplying a styloglossus muscle, genioglossus muscle 1405 or hyoglossus muscle 1410 as shown in FIG. 14. In some embodiments, the applied therapeutic stimulation improves a tone or function of the styloglossus, genioglossus or hyoglossus muscle. In some embodiments, the applied therapeutic stimulation prevents a relaxation of the styloglossus, genioglossus or hyoglossus muscle. In another embodiment, the applied stimulus prevents a patient's tongue from obstructing the patient's oropharyngeal airways.

In some embodiments, the therapeutic stimulation is characterized by the following stimulation parameters:
Frequency: ranging from 0.02 Hz to 10,000 Hz
Amplitude: ranging from 0.1 mA to 50 mA
Pulse width: ranging from 25 μs (microseconds) to 500 ms (milliseconds)
Duty cycle: ranging from 5% to 95%

In one embodiment the stimulation is an open-loop stimulation which is initiated by patients lying down and aborted when the patient wakes up. In some embodiments, the first and second pulse generators 525, 530 are controlled to generate and customize stimulation pulses using a computing device such as, but not limited to, a mobile phone, PDA, laptop or a smart-watch. The computing device transmits controlling instructions to the pulse generators through wireless communication. Using the computing device, the stimulation can be manually triggered by a patient or patient position detected by an inclinometer which may be physically coupled with one or more of the pulse generators 525, 530, in the computing device, or in another device positioned on the patient's body. The inclinometer is configured to trigger the stop and start of the stimulation. In some embodiments, a sensor is incorporated in the device 500 of the present specification to measure the patient's breathing while sleeping and to consequently modulate stimulation through the plurality of stimulating electrodes 525, 531. The sensor is one of $CO_2$ sensor or an $O_2$ sensor. The sensor is an accelerometer or a microphone configured to record and analyze a patient's breathing sounds, onset of snoring, or cessation of breathing. One or more of these sensors may detect an onset of an obstructive sleep apnea event and trigger the stimulus to prevent an episode of obstructive sleep apnea. The data from one or more of these sensors may be stored in the appliance 500 and/or wirelessly transmitted to a storage device such as a laptop, tablet device, or mobile phone to monitor a patient's sleep quality and quantify the severity of his/her sleep apnea and response to therapy.

In pre-deployment configuration the lingual bridge of the devices 200, 400 and 500 of FIGS. 2A, 2B, 2C, 4 and 5 has a first shape characterized by a first width '$w_1$' and a first height or arch '$h_1$'. In embodiments, the first shape is substantially arched or contoured to the patient's tongue and does not apply a significant or therapeutic pressure on the tongue. In post-deployment configuration the lingual bridge has a second shape characterized by a second width '$w_2$' and a second height or arch '$h_2$'. In embodiments, the second shape is substantially flat that applies a therapeutic level of pressure, such as level of pressure in a range of 0.01 to 5 psi, on the patient's tongue causing the tongue to move downward and/or forward thereby preventing the tongue from falling back into the oropharynx and obstructing while the patient is asleep. In embodiments, the lingual bridge is a mesh made of shape memory allow such as, but not limited to, Nitinol and is optionally coated with a soft membrane of silicone, PTFE, ePTFE, or a fabric. Thus, modification of the lingual bridge from the first shape to the second shape is affected by a change in temperature from room temperature or below to body temperature within the patient's mouth.

In some embodiments, the lingual bridge of the devices 200, 400 and 500 of FIGS. 2A, 2B, 2C, 4 and 5 is a full Nitinol mesh that changes from the first shape (in pre-deployment stage) to the second shape (in post-deployment stage) when positioned within the patient's mouth. In embodiments, the second width '$w_2$' is greater than the first width '$w_1$' while the second height '$h_2$' is lesser than the first height '$h_1$' of the lingual bridge. In some embodiments, the lingual bridge is characterized by an increase of up to 500% from the first width to the second width and a decrease of up to 400% from the first height to the second height. Notwithstanding the above, it should be appreciated that the relative dimensions will be customized to each patient and will be based on the individual's particular tongue and oral cavity shape and size. In another embodiment, the lingual bridge will be manufactured in a range of fixed or default sizes, such as 2-7, and a patient will first be fitted with a device having a default size closest to the patient's tongue and oral cavity shape and size. The default or fixed size device will then be modified to be customized to the patient's tongue and oral cavity shape and size. In another embodiment, the lingual bridge is shaped or sized to an individual patient's anatomy.

Figure 6A:
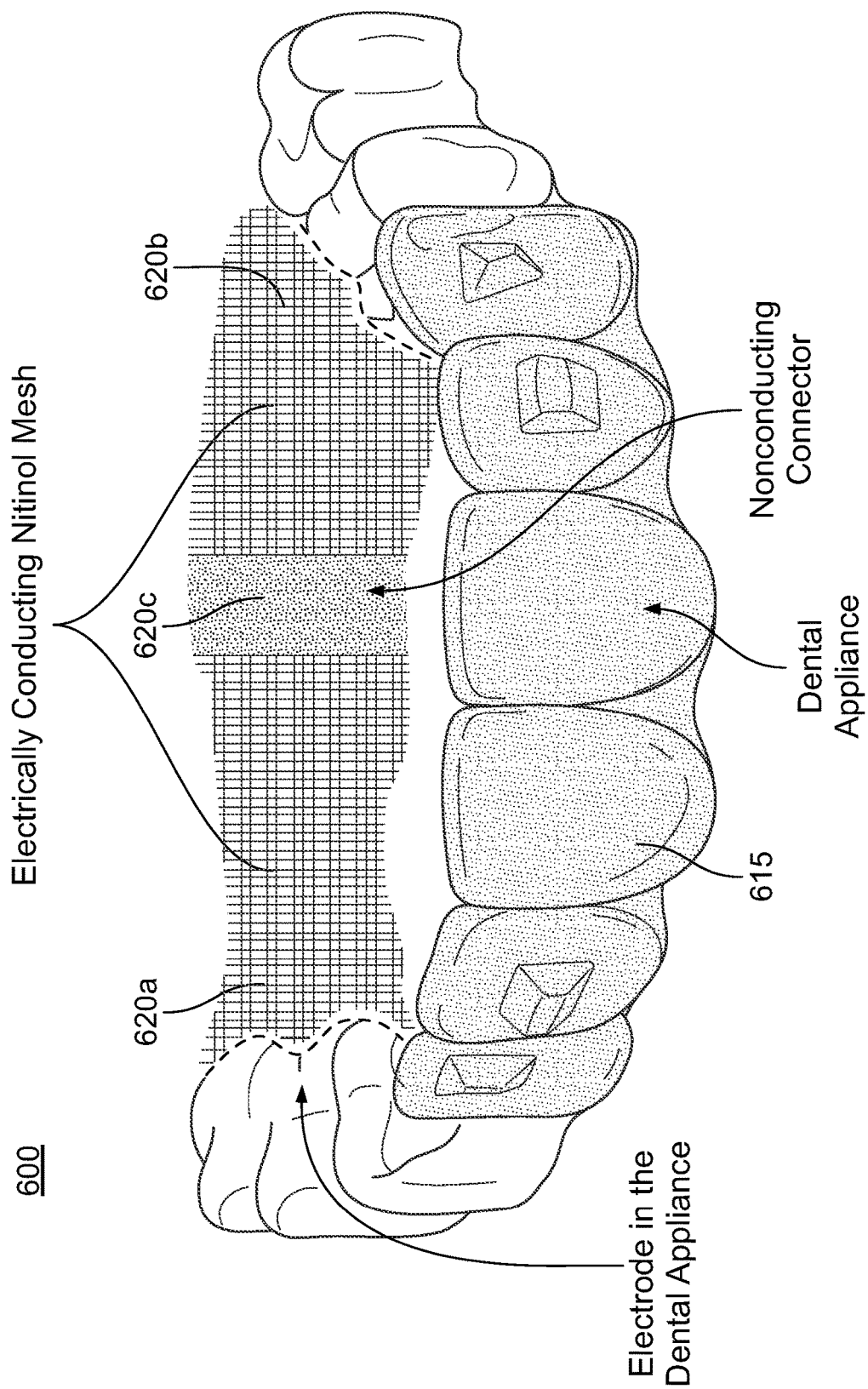
FIG. 6A shows a device for treating obstructive sleep apnea, in accordance with some embodiments of the present specification.
Figure 6B:
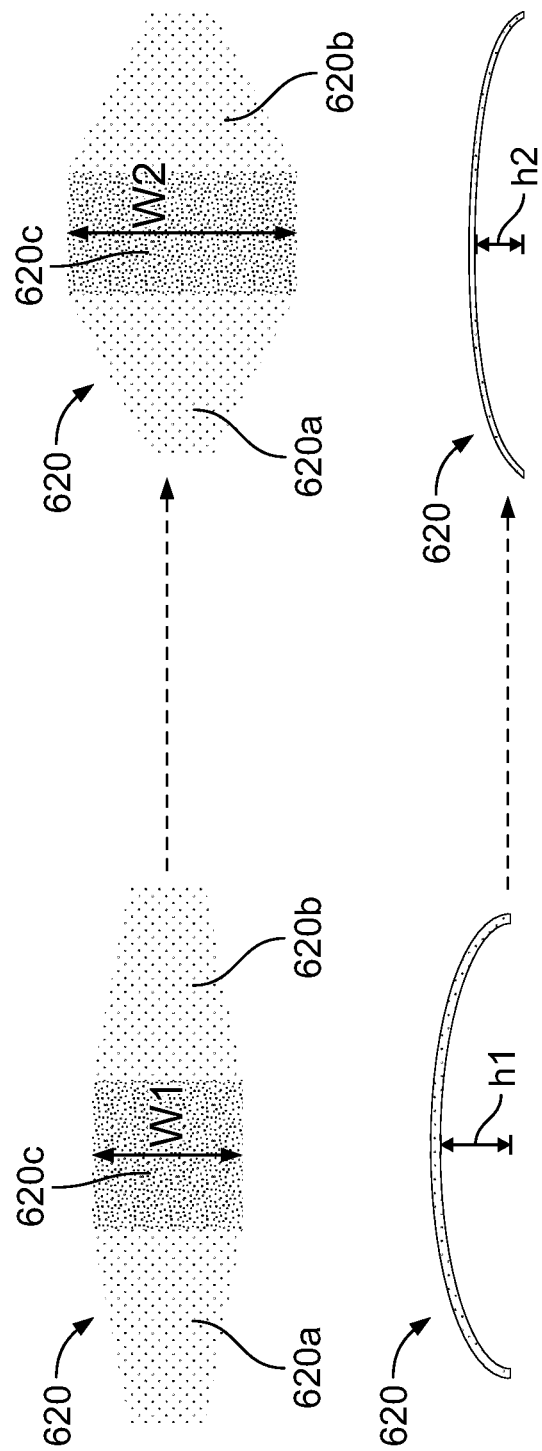
FIG. 6B illustrates modification of a lingual bridge from a first shape to a second shape, in accordance with some embodiments of the present specification.
Figure 6D:
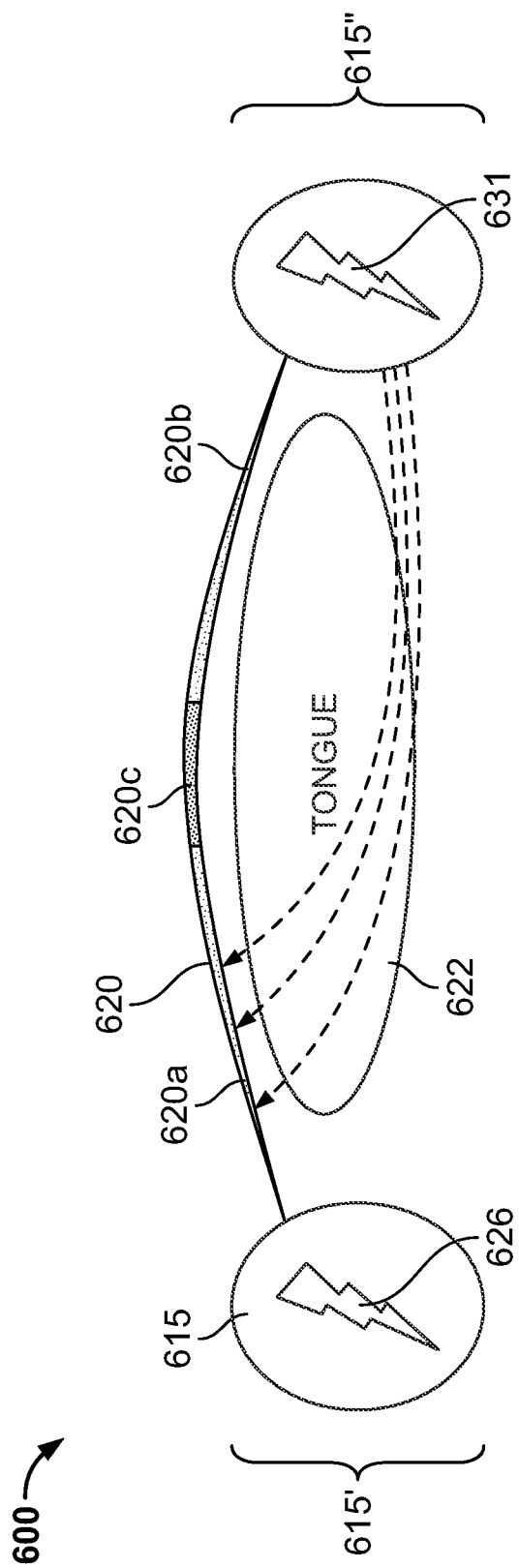
FIG. 6D illustrates flow of electrical stimulation from a plurality of electrodes through the patient's tongue to a contralateral half of the lingual bridge of FIG. 6B, in accordance with some embodiments of the present specification.

FIG. 6A shows another device 600 for treating obstructive sleep apnea, FIG. 6B shows a lingual bridge having a non-conducting portion, while FIGS. 6C and 6D show the device 600 positioned in a patient's oral cavity, in accordance with some embodiments of the present specification. Referring to FIGS. 6A, 6B, 6C and 6D, the device 600 comprises a dental appliance, component or fixture 615 and a lingual bridge 620. The dental appliance 615 is configured in accordance with any one of the embodiments of the present specification. In one embodiment (see FIG. 6C), the dental appliance 615 has first and second portions 615', 615". The first portion 615' comprises first, second and third hoop or loop structures 616 that are custom shaped and sized to girdle, hold or grip mandibular first, second and third molars, respectively, of the right mandibular dental arcade. The second portion 615" comprises first, second and third hoop or loop structures 616 that are custom shaped and sized to girdle, hold or grip mandibular first, second and third molars, respectively, of the left mandibular dental arcade.

In accordance with an embodiment, the lingual bridge 620 has first and second lingual portions 620a, 620b with an intervening third lingual portion 620c positioned between the first and second lingual portions 620a, 620b. The first and second lingual portions 620a, 620b are made of an electrically conducting mesh of a shape memory allow such as, but not limited to, Nitinol. The third lingual portion 620c is made of an electrically non-conducting area, mesh or web of material such as, but not limited to, PTFE, silk, polyester, or any other biocompatible material. In a pre-deployment configuration (that is, when not positioned within the patient's oral cavity) the lingual bridge 620 has a first shape characterized by a first width '$w_1$' and a first height or arch '$h_1$'. First height or arch '$h_1$' is defined as the distance from a bottom surface of the lingual bridge 620, when in a pre-deployment configuration, to a top surface of a tongue 622 of the patient. In embodiments, the first shape is arched or contoured to the patient's tongue 622 and does not apply a significant pressure on the tongue 622. In a post-deployment configuration (that is, when positioned within the patient's oral cavity and while the patient is asleep) the lingual bridge 620 has a second shape characterized by a second width '$w_2$' and a second height '$h_2$'. Second height or arch '$h_2$' is defined as the distance from a bottom surface of the lingual bridge 620, when in a post-deployment configuration, to a top surface of a tongue 622 of the patient. In embodiments, the second shape is flattened such that the lingual bridge 620 applies a therapeutic level of pressure, such as 0.01 psi to 5 psi, on the tongue 622 causing the tongue 622 to move downward and/or forward thereby preventing the tongue 622 from falling back while the patient is asleep.

In embodiments, the second width '$w_2$' is greater than the first width '$w_1$' while the second height '$h_2$' is lesser than the first height '$h_1$' of the lingual bridge 620. In one embodiment, both the width and the height range from 5 mm to 5 cm. In some embodiments, the lingual bridge 620 is characterized by an increase of up to 500% from the first width to the second width and a decrease of up to 400% from the first height to the second height. In some embodiments, the lingual bridge 620 has a narrow oval shape (or, as above, rectangular, polygonal, or any freeform shape) that increases in width as the lingual bridge 620 changes from the first shape in the pre-deployment configuration to the second shape in the post-deployment configuration. In some embodiments, the intervening third lingual portion 620c has a rectangular shape and the first and second lingual portions 620a, 620b have trapezoidal shapes with smaller ends tapering toward the sides of the mouth. In some embodiments, the shape of the lingual portions 620c, 620b, and 620c can be modified to fit patient's anatomy or desired electrical field for optimal therapeutic effect.

In an embodiment, a first pulse generator with associated one or more stimulating electrodes 626 is incorporated in the first portion 615' and a second pulse generator with associated one or more stimulating electrodes 631 is incorporated in the second portion 615" of the dental appliance 615 (as shown in FIG. 6D). The first and second lingual portions 620a, 620b of the lingual bridge 620 respectively comprise the electrodes 626, 631 and the intervening lingual portion 620c prevents the electrodes 626, 631 from shorting. In embodiments, the first and second pulse generators and stimulating electrodes 626, 631 apply therapeutic stimulation to one of a styloglossus, genioglossus or hyoglossus muscle or to a nerve supplying a styloglossus, genioglossus muscle 1405 or hyoglossus muscle 1410 as shown in FIG. 14. In some embodiments, the applied therapeutic stimulation improves a tone or function of the styloglossus, genioglossus or hyoglossus muscle. In some embodiments, the applied therapeutic stimulation prevents a relaxation of the styloglossus, genioglossus, or hyoglossus muscle. In some embodiments, the applied therapeutic stimulation prevents a styloglossus, genioglossus or hyoglossus muscle from blocking a patient's oropharyngeal airway.

As shown in FIGS. 6C and 6D, when applied, therapeutic electrical stimulation from the first pulse generator and electrodes 626 in the first portion 615' flows to the contralateral half of the lingual bridge 620—that is, to the second lingual portion 620b—thereby causing the stimulation pulses or stimulating electric field to be forced through the tongue 622 to stimulate a styloglossus, genioglossus or hyoglossus muscle or nerve supplying a styloglossus, genioglossus or hyoglossus muscle in a first direction and stimulating the lingual tissue and nerves. Similarly, when applied, therapeutic electrical stimulation from the second pulse generator and electrodes 631 in the second portion 615" flows to the contralateral half of the lingual bridge 620—that is, to the first lingual portion 620a—thereby causing the stimulation pulses or stimulating electric field to be forced through the tongue 622 to stimulate a styloglossus, genioglossus or hyoglossus muscle or nerve supplying a styloglossus, genioglossus or hyoglossus muscle in a second direction (substantially opposite to the first direction) and stimulating the lingual tissue and nerves. This unique electrode design allows for simultaneously using the mechanical and electrical therapeutic effect with the lingual bridge 620. In some embodiments, additional electrodes can be incorporated to optimize the electrical field for desired therapeutic effect. The stimulation can be titrated to a tolerable stimulation level. In one embodiment, the stimulation is at a level that is not perceived by the patient.

In various embodiments, the lingual bridge 620 is a mesh made of shape memory allow such as, but not limited to, Nitinol and is optionally coated with a soft membrane of silicone, PTFE, ePTFE, or a fabric. Thus, a change in shape of the lingual bridge 620 is affected by a change in temperature from room temperature to body temperature within the patient's mouth. In various embodiments, the dental appliance 615 is custom designed to fit the patient's teeth or dental arcade.

Figure 7B:
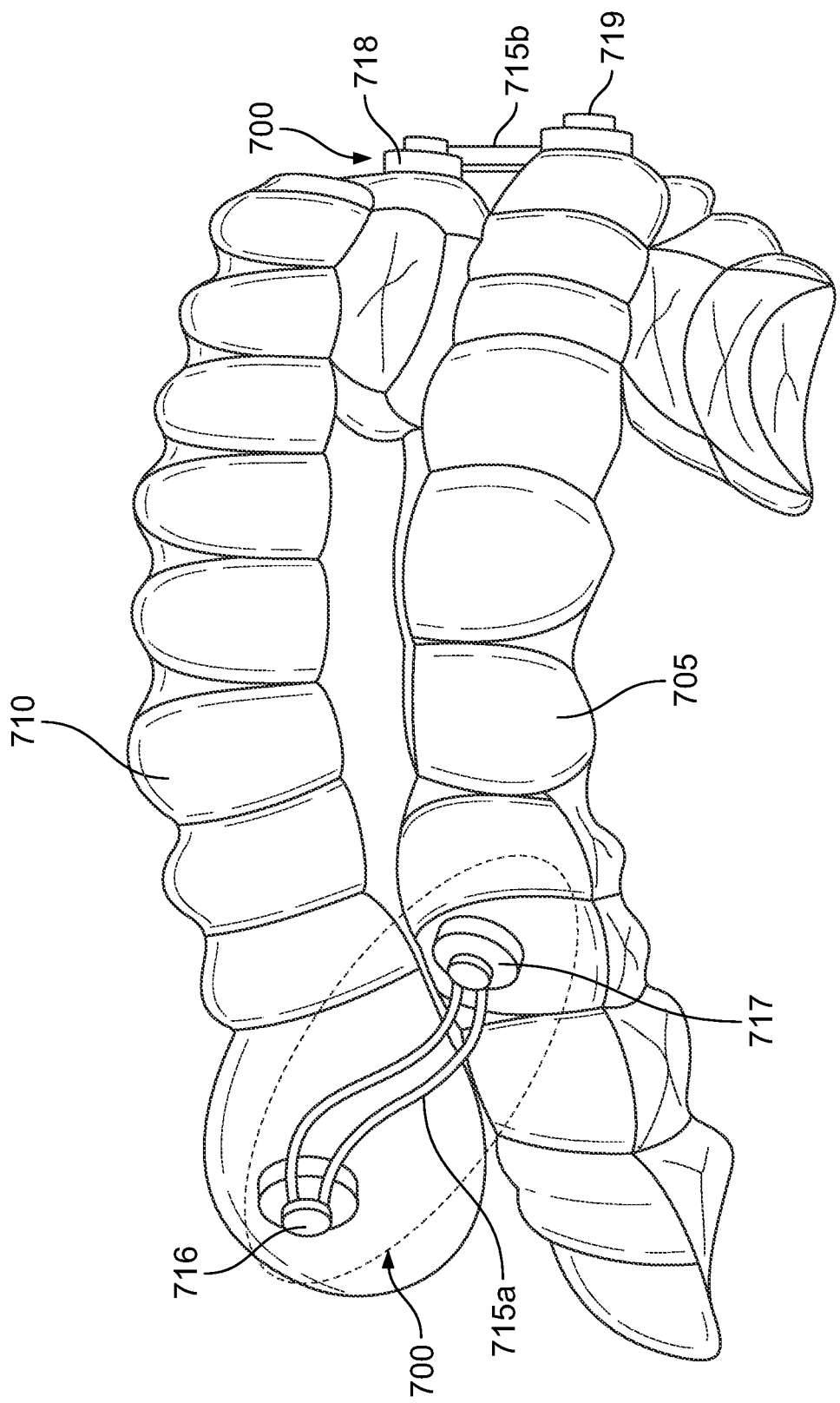
FIG. 7B shows a first perspective view of the device of FIG. 7A positioned in a patient's oral cavity, in accordance with some embodiments of the present specification.
Figure 7C:
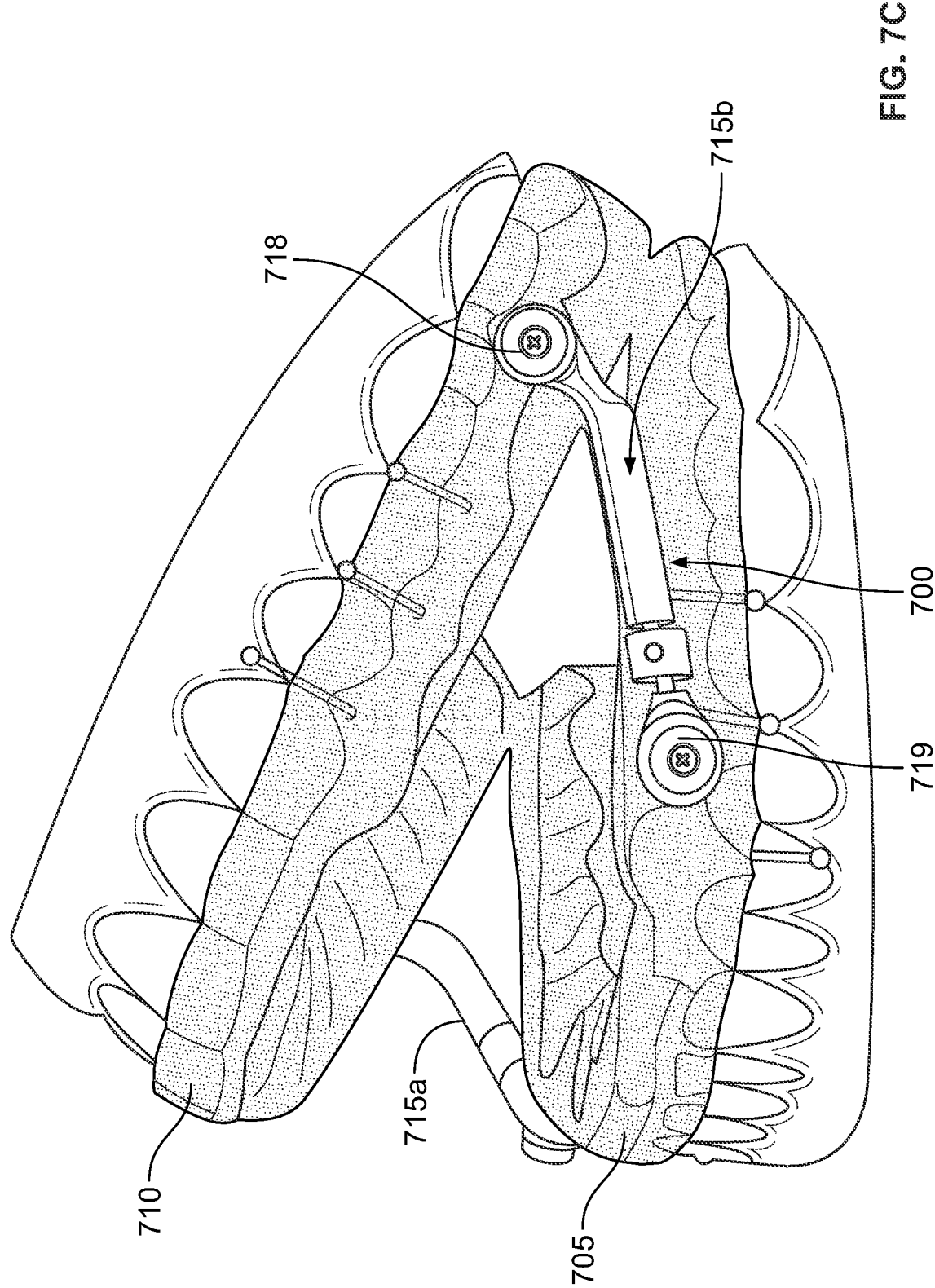
FIG. 7C shows a second perspective view of the device of FIG. 7A positioned in the patient's oral cavity, in accordance with some embodiments of the present specification.

FIG. 7A shows first and second side views 705, 710 of a device 700 for treating obstructive sleep apnea while FIGS. 7B and 7C show various perspective views of the device 700, in accordance with some embodiments. The first view 705 of FIG. 7A shows the device 700 in a pre-deployment configuration (that is, when not positioned within the patient's oral cavity) while the second view 710 shows the device 700 in a post-deployment configuration (that is, when positioned within the patient's oral cavity and while the patient is asleep). Referring now to FIGS. 7A, 7B and 7C, the device 700 comprises a lower jaw or mandibular appliance 705, an upper jaw or maxillary appliance 710, a first connector 715a having an upper end 716 coupled to the upper jaw appliance 710 and a lower end 717 coupled to the lower jaw appliance 705, and a second connector 715b having an upper end 718 coupled to the upper jaw appliance 710 and a lower end 719 coupled to the lower jaw appliance 705. The first connector 715a is positioned on the right side and towards the buccal or lingual surface of the dental arcades, proximal the posterior ends of the lower and upper jaw appliances 705, 710. The second connector 715b is positioned on the left side and towards the buccal or lingual surface of the dental arcades proximal the posterior ends of the lower and upper jaw appliances 705, 710.

The lower and upper jaw appliances 705, 710 are custom shaped and sized to fix or grip onto and engage a patient's mandibular and maxillary dental arcades, respectively. In some embodiments, the appliances 705, 710 are heat sensitive and may be molded to custom fit the patient's teeth. In some embodiments, the connectors 715a, 715b are removable so they may be removed while the appliances 705, 710 are heated and molded to the patient's teeth. As shown in view 710 of FIG. 7A, once implanted or positioned within the patient's oral cavity, the first and second connectors 715a, 715b apply forward force on the lower jaw appliance 705 thereby pushing and extending the patient's lower jaw forward.

In some embodiments, as shown in FIGS. 7B and 7C, the first and second connectors 715a, 715b are made of a shape memory alloy such as, but not limited to, Nitinol which expand after being placed in the patient's oral cavity and exposed to a higher temperature in the patient's mouth to apply forward force on the patient's lower or mandibular jaw thereby, pushing it forward.

In other embodiments, referring to FIGS. 7B and 7C, the first and second connectors 715a, 715b are motorized components with pistons that apply a forward pressure on the lower jaw appliance 705 and therefore push and extend the patient's lower jaw forward. There are optional pressure sensors which are used to modify the force applied by the piston. The motorized component can be controlled wirelessly by a patient controller, laptop, tablet device, mobile phone, or any computing device.

In some embodiments, as discussed with reference to FIGS. 7E and 7F, each of the first and second connectors comprise telescoping outer and inner arms having magnetic components with magnetic repulsive forces that apply a forward pressure on the lower jaw appliance.

Referring to FIGS. 7B and 7C, in some embodiments, the upper ends 716, 718 of the connectors 715a, 715b are positioned on the upper jaw appliance 710 in a more posterior position, or further back in a patient's mouth, relative to the position of the lower ends 717, 719 of the connectors 715a, 715b on the lower jaw appliance 705. Positioned in such a way, when the connectors 715a, 715b expand through shape memory properties or extend via a motorized piston, the connectors 715a, 715b cause the lower jaw to move or extend forward.

Figure 7D:
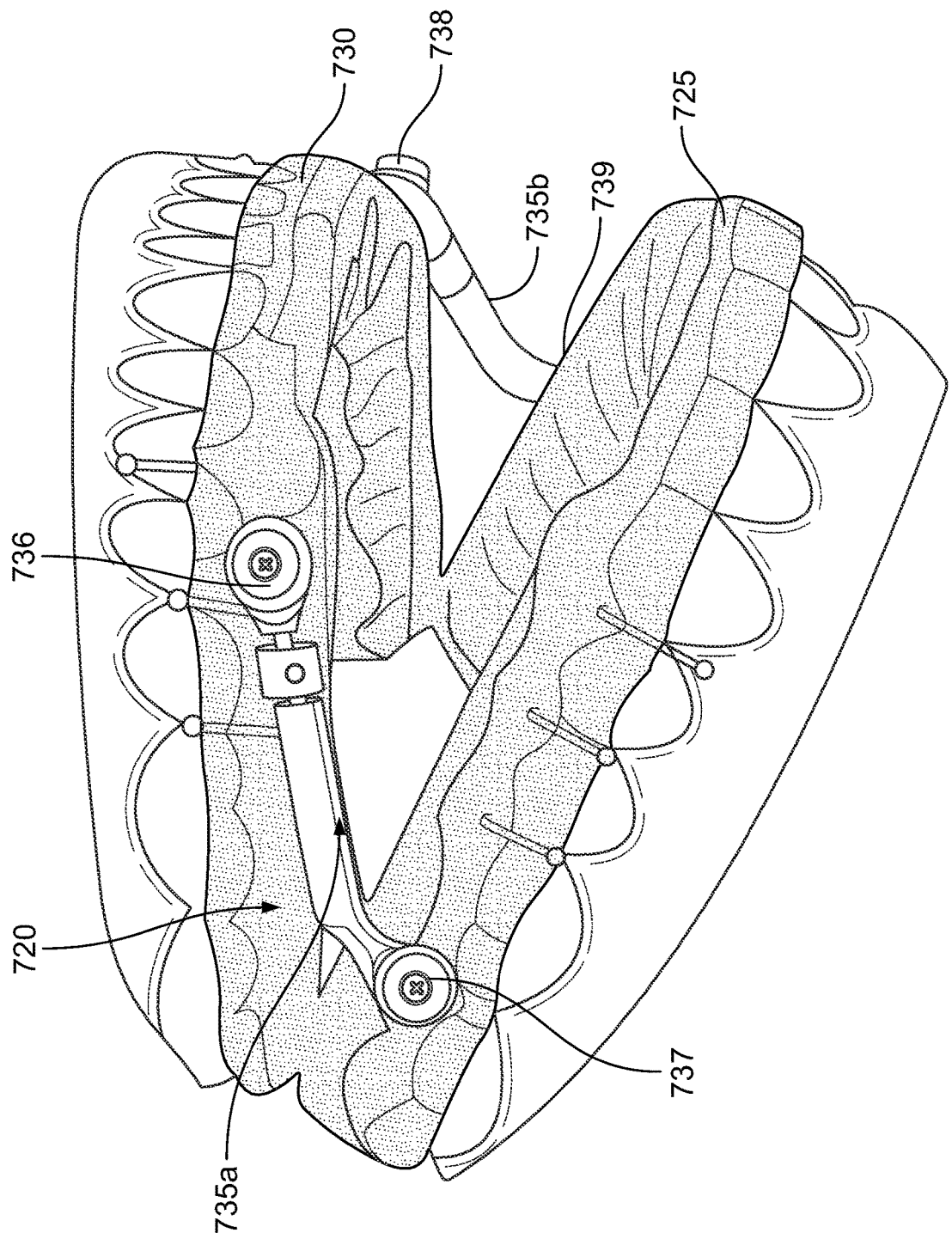
FIG. 7D shows a perspective view of another device for treating obstructive sleep apnea positioned in a patient's oral cavity, in accordance with some embodiments of the present specification.

FIG. 7D shows a perspective view of another device 720 for treating obstructive sleep apnea positioned in a patient's oral cavity, in accordance with some embodiments of the present specification. The device 720 is similar to those shown in FIGS. 7A and 7B with the connectors 735a, 735b attached to the upper and lower jaw appliances 730, 735 in different positions. Specifically, referring to FIG. 7D, in some embodiments, the upper ends 736, 738 of the connectors 735a, 735b are positioned on the upper jaw appliance 730 in a more anterior position, or further forward in a patient's mouth, relative to the position of the lower ends 737, 739 of the connectors 735a, 735b on the lower jaw appliance 725. In some embodiments, as shown in FIG. 7D, the first and second connectors 735a, 735b are made of a shape memory alloy such as, but not limited to, Nitinol which contract after being placed in the patient's oral cavity thereby pulling the patient's lower or mandibular jaw forward. In other embodiments, referring to FIG. 7D, the first and second connectors 735a, 735b are motorized components with pistons that apply a forward pressure on the lower jaw appliance 725 and therefore pull and extend the patient's lower jaw forward. Positioned in such a way, when the connectors 735a, 735b contract through shape memory properties or contract via a motorized piston, the connectors 735a, 735b cause the lower jaw to move or extend forward. There are optional pressure sensors which are used to modify the force applied by the motorized piston. The motorized components can be controlled wirelessly by a patient controller, laptop, tablet device, mobile phone, or any computing device. In some embodiment, the shape memory component is a removal insert that can be exchanged out over time to increase or decrease the length of the connector. In some embodiments, as discussed with reference to FIGS. 7E and 7F, each of the first and second connectors comprise telescoping outer and inner arms having magnetic components with magnetic repulsive forces that apply a forward pressure on the lower jaw appliance.

Figure 7E:
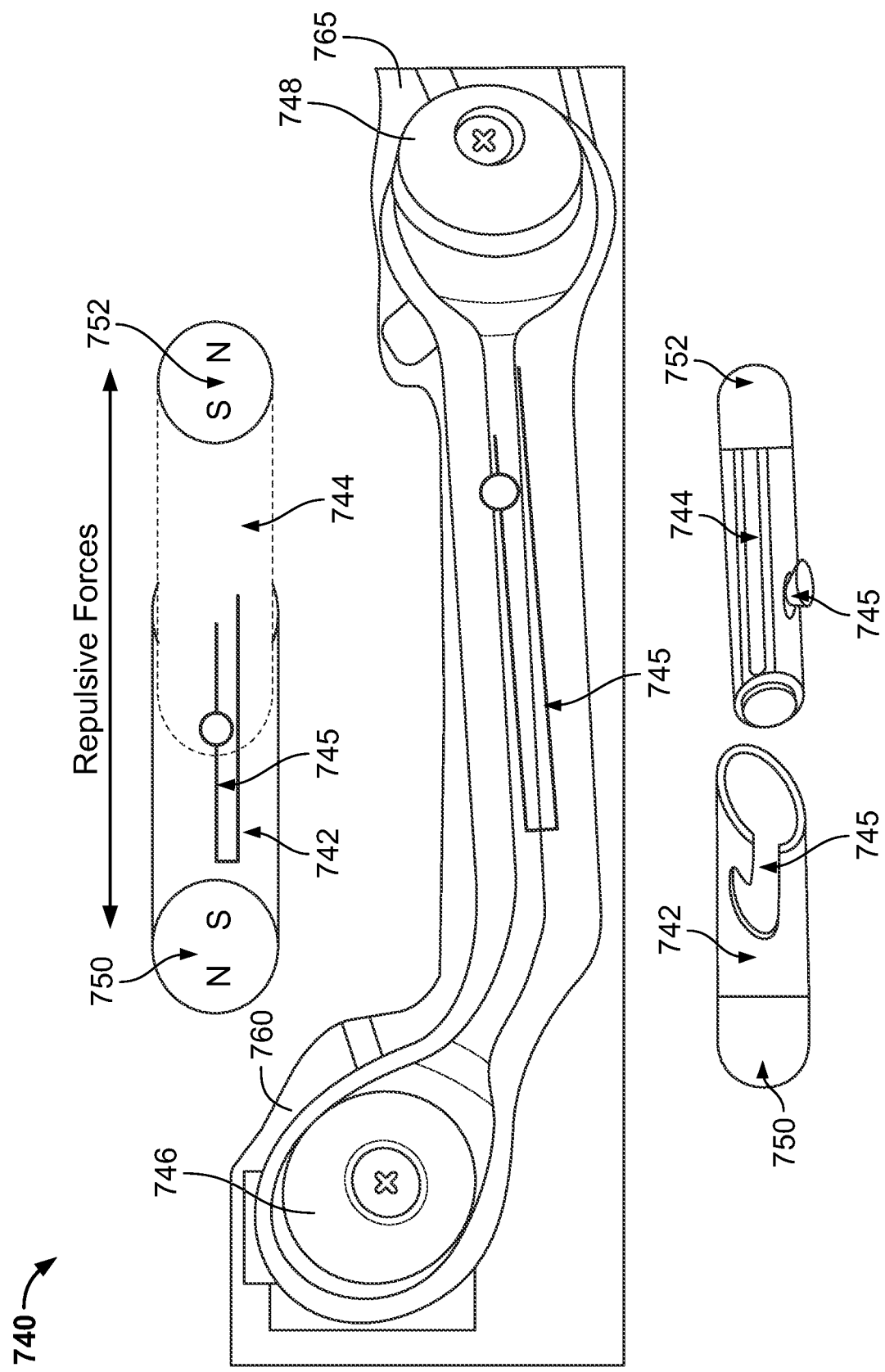
FIG. 7E shows a connector that uses magnetic force to apply forward pressure to a patient's lower or mandibular jaw, in accordance with some embodiments of the present specification.
Figure 7F:
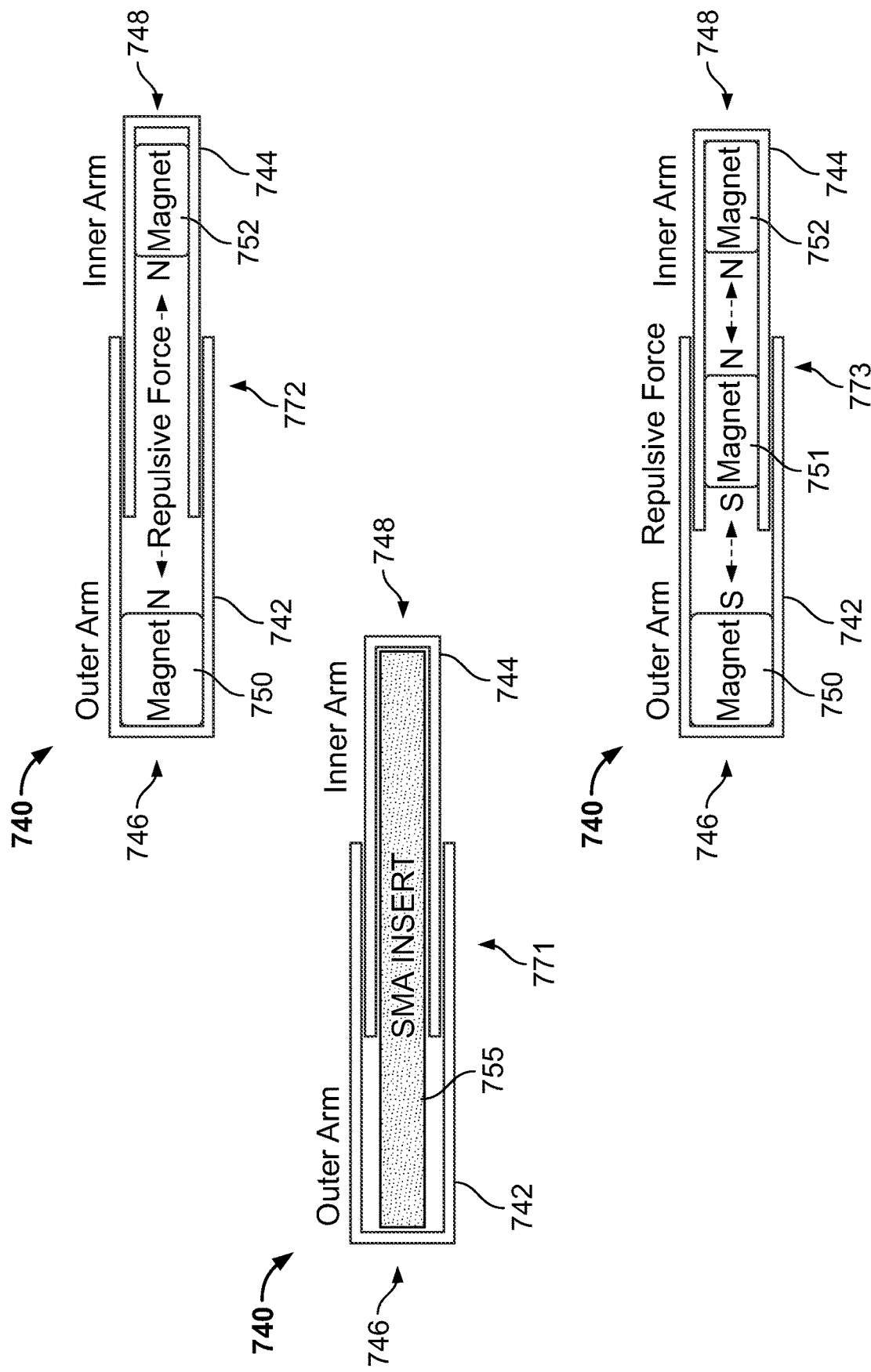
FIG. 7F shows first, second and third embodiments of the connector of FIG. 7E.

FIGS. 7E and 7F show a connector 740 that uses magnetic force to apply forward pressure to the patient's lower or mandibular jaw, in accordance with some embodiments of the present specification. A first connector 740 is configured to be positioned on a first side of a patient's oral cavity, attached to a jaw or dental appliance, and, in some embodiments, a second connector 740 is configured to be positioned on a second side, opposite the first side, of the patient's oral cavity, attached to a jaw or dental appliance. The connector 740 has telescoping outer and inner (or first and second) members or arms 742, 744 such that the two arms 742, 744 can slide and extend relative to each other thereby modulating a length of the connector 740. The arms 742, 744 form a sliding joint with a substantially U-shaped groove 745 that enables the two arms 742, 744 to be disconnected, disengaged or uncoupled and reconnected, reengaged or recoupled when needed.

In embodiments, the two arms 742, 744 are hollow or partially hollow. When coupled together, the outer arm 742 has a first end 746 while the inner arm 744 has a second end 748 opposite to the first end 746. In embodiments, the first end 746 is attached to an upper jaw appliance 760 and the second end 748 is attached to a lower jaw appliance 765. In other embodiments, the first end 746 is attached to a lower jaw appliance and the second end 748 is attached to an upper jaw appliance. The first member and second member are not attached to a same one of the lower jaw appliance or the upper jaw appliance. In embodiments, the lower jaw appliance 765 is configured to engage a patient's mandibular dental arcade and the upper jaw appliance 760 is configured to engage a patient's maxillary dental arcade. In some embodiments, as shown in FIG. 7E and view 772 of FIG. 7F, a first magnet 750 is positioned at or proximate the first end 746 while a second magnet 752 is positioned at or proximate the second end 748 within the arms 742, 744 (in embodiments, the arms 742, 744 are disconnected to insert the first and second magnets 750, 752 in position and reconnected thereafter). The first and second magnets 750, 752 are oriented such that their like poles face each other. That is, either north poles or south poles of the first and second magnets 750, 752 face each other. Consequently, a repulsive magnetic force between the first and second magnets 750, 752 is used to push and slide the two arms 742, 744 relative to each other thereby extending the length of the connector 740.

The repulsive magnetic force between the outer and inner arms 742, 744 can be customized to individual patient's therapeutic need by changing the strength, size and/or number of magnets. For example, in some embodiments, as shown in view 773 of FIG. 7F a third magnet 751 is positioned within the arms 742, 744 so as to lie between the first and second magnets 750, 752. The first and third magnets 750, 751 are oriented such that their respective like poles face each other while the third and second magnets 751, 752 are also oriented such that their respective like poles face each other. Consequently, repulsive magnetic forces act between the first and third magnets 750, 751 and the third and second magnets 751, 752 that push and slide the two arms 742, 744 relative to each other thereby extending the length of the connector 740. In some embodiments, a second connector, positioned in a patient's oral cavity on a side opposite a first connector 740, also includes outer and inner (or third and fourth) arms or members with fourth, fifth, and sixth magnets which function in a like manner to the arms and magnets of connector 740 to assist with treating sleep apnea.

In various embodiments, first and second connectors that are similar to the connectors used in the embodiments of FIGS. 7A through 7D such that the first and second ends 746, 748 of each of the first and second connectors are respectively connected to an upper jaw appliance and a lower jaw appliance. In some embodiments, a first connector is positioned on a left buccal surface of a patient's dental arcades. In some embodiments, a second connector is positioned on a right buccal surface of a patient's dental arcades. In some embodiments, only one connector is used, though this is not preferred. If only one connector is used, it is positioned in the center of a patient's oral cavity such that a top end of the connector is positioned proximate the patient's central/lateral incisors and the bottom connector is positioned proximate the patient's bottom incisors. Once implanted or positioned within the patient's oral cavity, the first and second connectors apply forward magnetic force on the lower jaw appliance thereby pushing and extending the patient's lower jaw forward. As the muscle tone diminishes over time during different phases of sleep, the muscle resistance to the repulsive magnetic force being applied to the connector 740 decreases thereby lengthening the connector 740 and pushing the mandible further out and improving the efficacy of the device during the most vulnerable period for sleep apnea. Thus, the dynamic length adjust to the patient's muscle tone which changes with sleep and the connector 740 has the longest length when the muscle tone is lowest and the sleep apnea risk in highest.

In some embodiments, as shown in view 771 of FIG. 7F, the arms 742, 744 are uncoupled to add one or more inserts 755 of shape memory alloy such as, but not limited to, Nitinol, which lengthens after being placed in the patient's oral cavity, thereby pushing the patient's lower or mandibular jaw forward. The one or more inserts 755 could be changed over time to achieve a desired therapeutic effect in an individual patient.

Both the magnetic and shape memory insert embodiments enable a dynamic length and distance connector compared to prior art connectors that are fixed length mechanical connectors which use screws to tighten and loosen the dental appliance. It should be appreciated that the dental appliance or device with various connector embodiments of FIGS. 7A through 7F, maintain mandibular advancement while permitting lateral jaw movement, jaw opening, or jaw closing, thereby reducing the risk of complications and therefore achieve better patient compliance.

In various embodiments, each of the embodiments of the dental appliance/device as well as the connectors of FIGS. 7A through 7F can be integrated with the embodiments of tongue implants and dental appliances/implants disclosed with reference to FIGS. 8A through 8D, 9, 10, 11, 12A, 12B, 13A, 13B, and 15A through 15G. In still other embodiments, each of the embodiments of the dental appliance/device as well as the connectors of FIGS. 7A through 7F further include a lingual bridge similar to the embodiments disclosed with reference to FIGS. 1A through 1D, 2A through 2C, 4, 5, and 6A through 6D. In still other embodiments, each of the embodiments of the dental appliance/device as well as the connectors of FIGS. 7A through 7F further include at least one pulse generator and associated one or more electrodes similar to the embodiments disclosed with reference to FIGS. 5 and 6A through 6D.

Figure 8A:
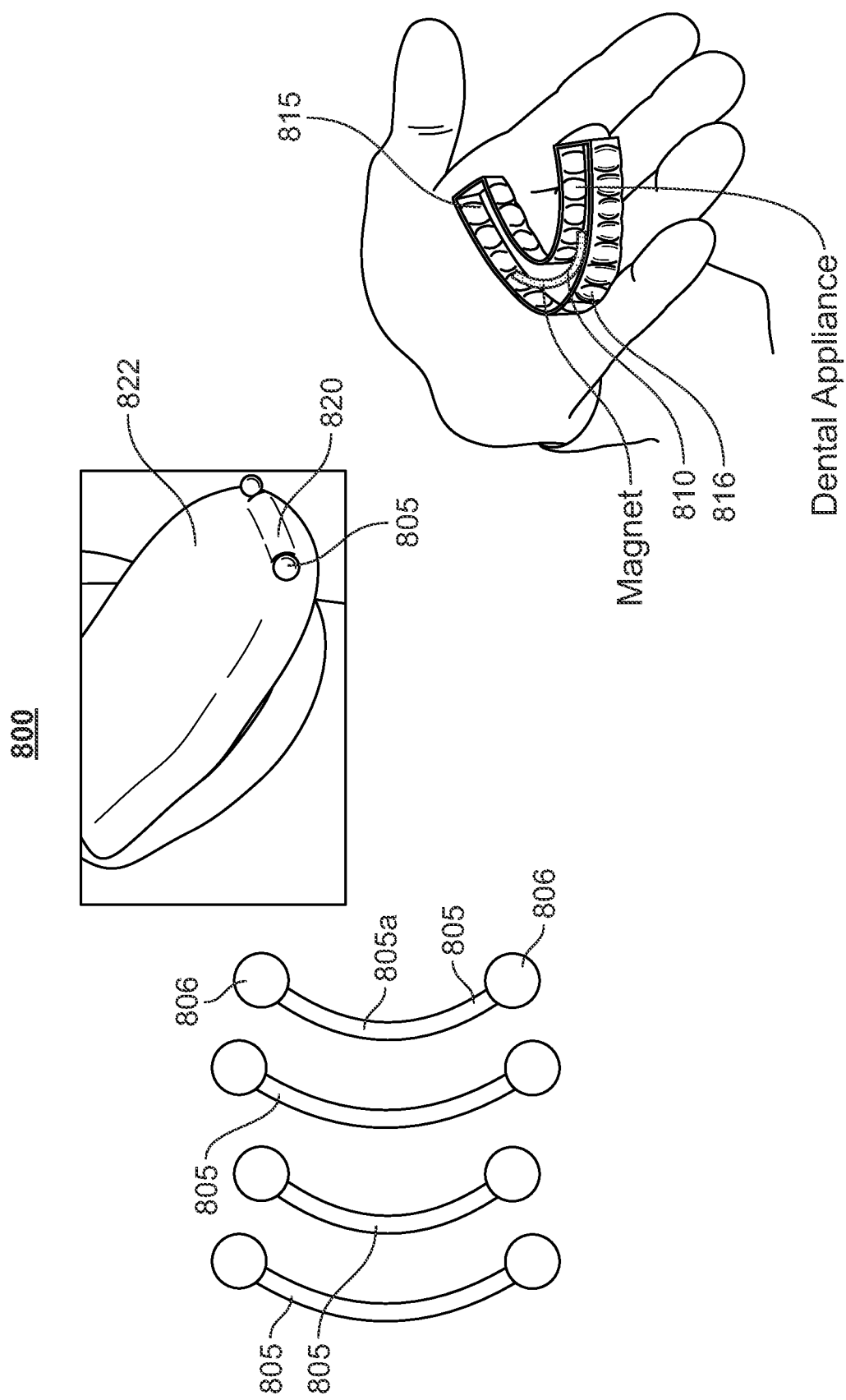
FIG. 8A shows elements of a device that work together through magnetic forces, in accordance with some embodiments of the present specification.

In accordance with some aspects, the present specification discloses embodiments of tongue implants and dental appliances/implants which work together through magnetic forces to move the tongue. FIG. 8A shows elements of a device 800 that work together through magnetic forces, in accordance with some embodiments of the present specification. The device 800 comprises a first element 805 affixed to or implantable in a patient's tongue 822 and a second element 810 configured as a dental implant. In some embodiments, the second element 810 is incorporated or supported within a third element 815 configured as a dental appliance to engage the patient's teeth. In some embodiments, the third element or appliance 815 is heat sensitive and may be molded to custom fit the patient's teeth. In some embodiments, the second element 810 is removable so it be removed while the appliance is heated and molded to the patient's teeth.

The first element or lingual implant 805 comprises a curved wire 805a with stops, plugs or rivets 806 at first and second ends of the wire 805a. When implanted in the patient's tongue 822, the stops, plugs or rivets 806 prevent the first element 805 from getting dislodged from an implanted position. In some embodiments, the first element 805 is implanted proximal a tip or anterior portion 820 of the tongue 822. In some embodiments, the stops, plugs or rivets 806 have substantially spherical shapes.

In some embodiments, the third element 815 is configured as an upper jaw appliance (similar to the upper jaw appliance 710 of FIGS. 7B, 7C and 7D) custom shaped and sized to fix or grip onto and engage a patient's maxillary dental arcade. In another embodiment, the third element 815 may be positioned on either the maxillary dental arcade or over the mandibular dental arcade. The second element 810 configured as the dental implant has a curvilinear form and is incorporated, positioned or supported at an anterior end 816 of the third element 815.

In some embodiments, as shown in FIG. 8B, the first element 805 is positioned as an intra-lingual implant in the patient's tongue 822 proximal the tip or anterior portion 820 while the second element or magnetic dental implant 810 is positioned at the anterior end of the dental appliance 815 (FIG. 8A). Also shown are exemplary magnetic lines of forces 830b acting on the first element 805.

In some embodiments, as shown in FIG. 8C, the first element 805 is positioned as a sub-lingual implant in the patient's tongue 822 proximal the tip or anterior portion 820 while the second element or magnetic dental implant 810 is positioned at the anterior end of the dental appliance 815 (FIG. 8A). Also shown are exemplary magnetic lines of forces 830c acting on the first element 805.

In some embodiments, as shown in FIG. 8D, the first element 805 is positioned as a trans-lingual implant in the patient's tongue 822 proximal the tip or anterior portion 820 while the second element or magnetic dental implant 810 is positioned at the anterior end of the dental appliance 815 (FIG. 8A). Also shown are exemplary magnetic lines of forces 830d acting on the first element 805. In embodiments, the magnetic lines of forces 830b, 830c and 830d between the first and second elements 805, 810 cause the patient's tongue 822 to be pulled forward anteriorly to keep the patient's airway 802 open.

Figure 9:
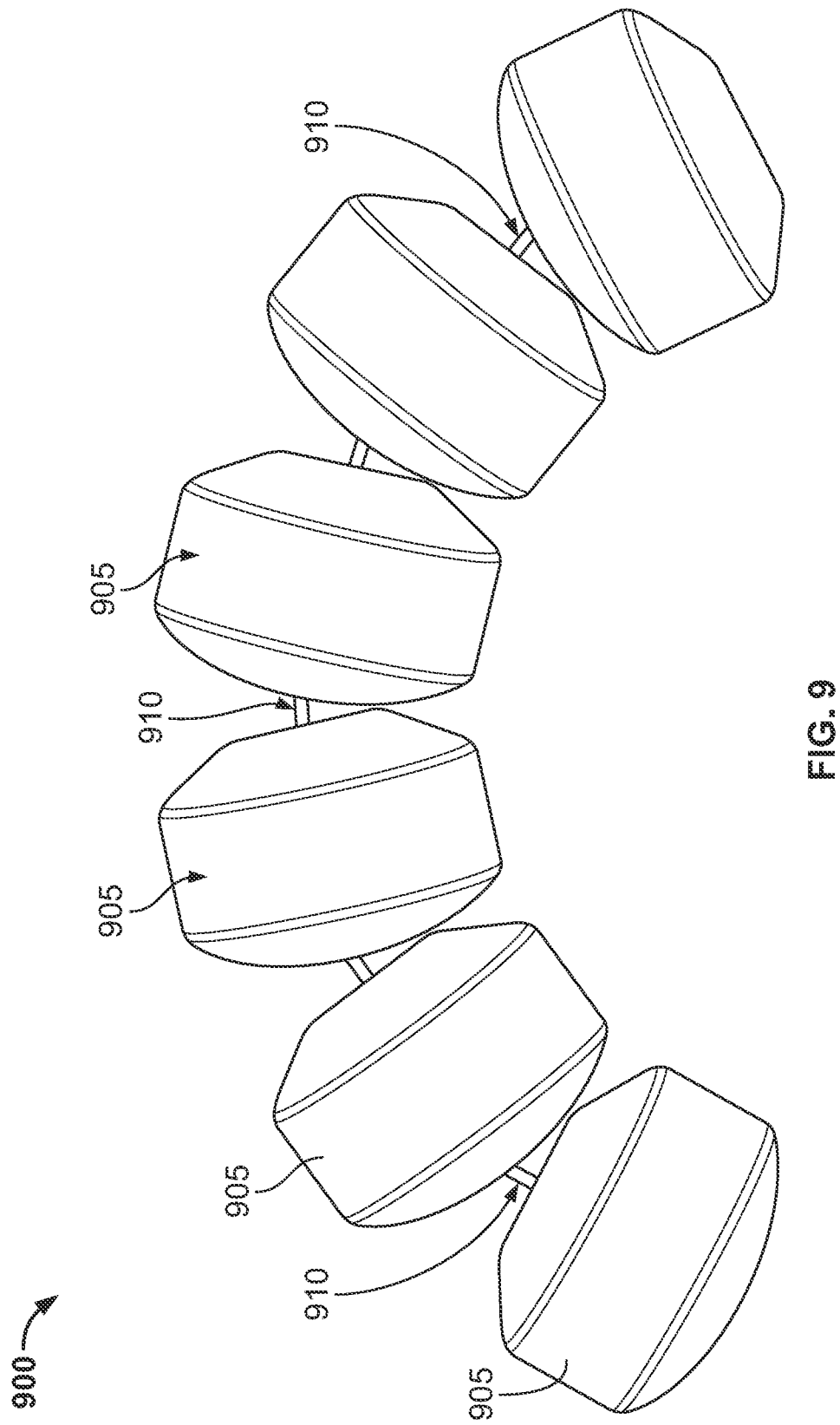
FIG. 9 shows a perspective view of a lingual implant, in accordance with some embodiments of the present specification.

FIG. 9 shows a perspective view of a lingual implant 900, in accordance with some embodiments of the present specification. The lingual implant 900 comprises a plurality of atraumatic ferromagnetic implants or rare earth magnets or elements 905 connected by a plurality of flexible/articulating connectors 910. The ferromagnetic implants or rare earth magnets or elements 905 have a dimension between 1 mm and 10 mm each and each of the connecting elements 910 are also 1-10 mm. The flexible connectors 910 allow each of the plurality of implants or elements 905 to move relative to each other and adjust to the shape or contour of a patient's tongue while also allowing for movement of the tongue muscles.

Figure 10:
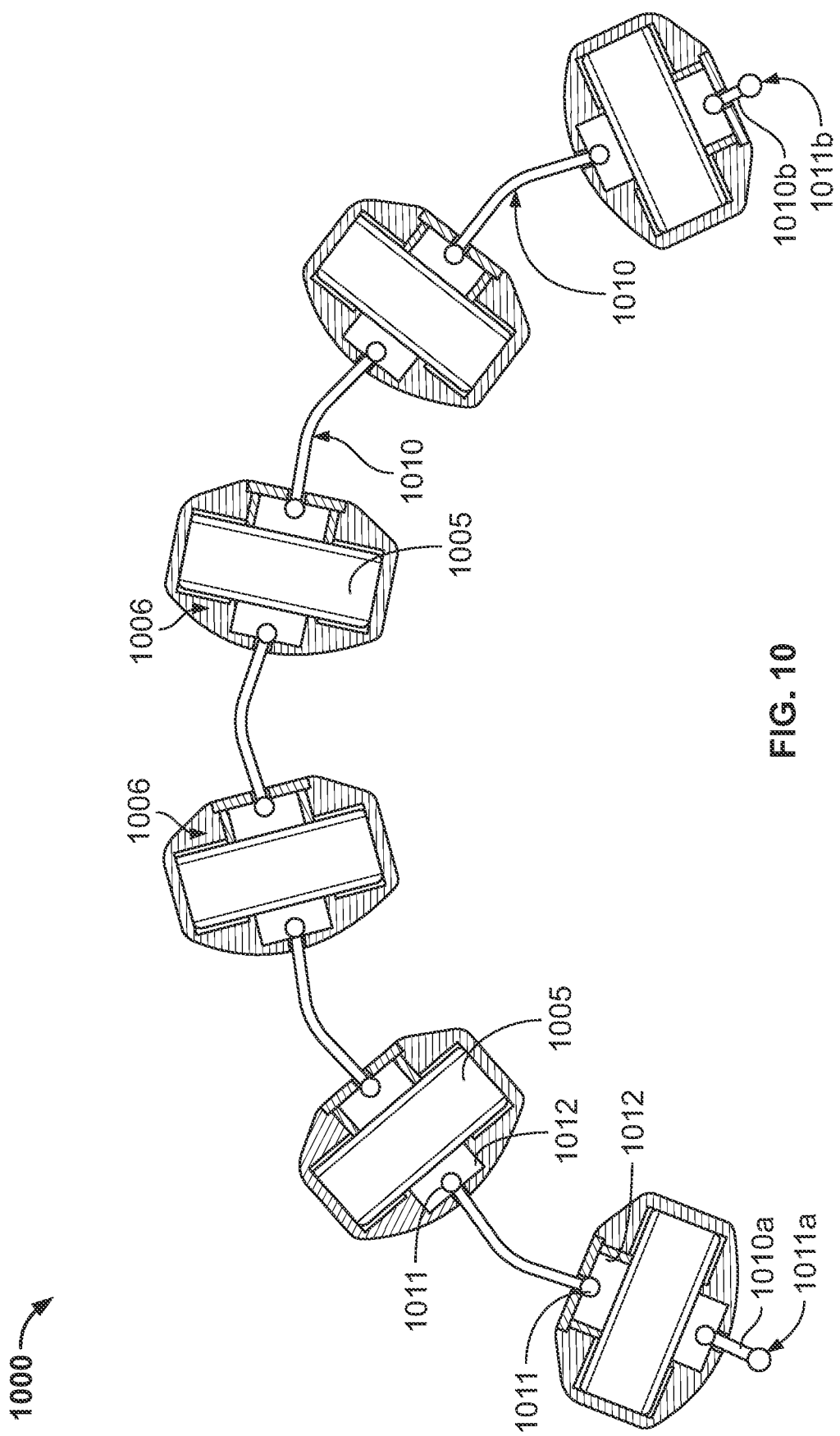
FIG. 10 shows an exploded view of a dental implant, in accordance with some embodiments of the present specification.

FIG. 10 shows an exploded view of a magnetic dental implant 1000, in accordance with some embodiments of the present specification. The dental implant 1000 comprises a plurality of rare-earth magnetic elements 1005 connected by a plurality of flexible/articulating connectors 1010. The flexible connectors 1010 allow each of the plurality of magnetic elements 1005 to move relative to each other. In some embodiments, each of the plurality of connectors 1010 has first and second connector balls 1011 at its ends. The connector balls 1011 fit into corresponding sockets 1012 of the plurality of magnetic elements 1005 to form ball and socket joints. The first and second end connectors 1010a, 1010b have connector balls 1011a, 1011b at the free ends to enable additional magnetic elements 1005 to be connected in order to modify the magnetic strength of the dental implant 1000. In some embodiments, each of the plurality of magnetic elements 1005 has a biocompatible coating 1006.

Figure 11:
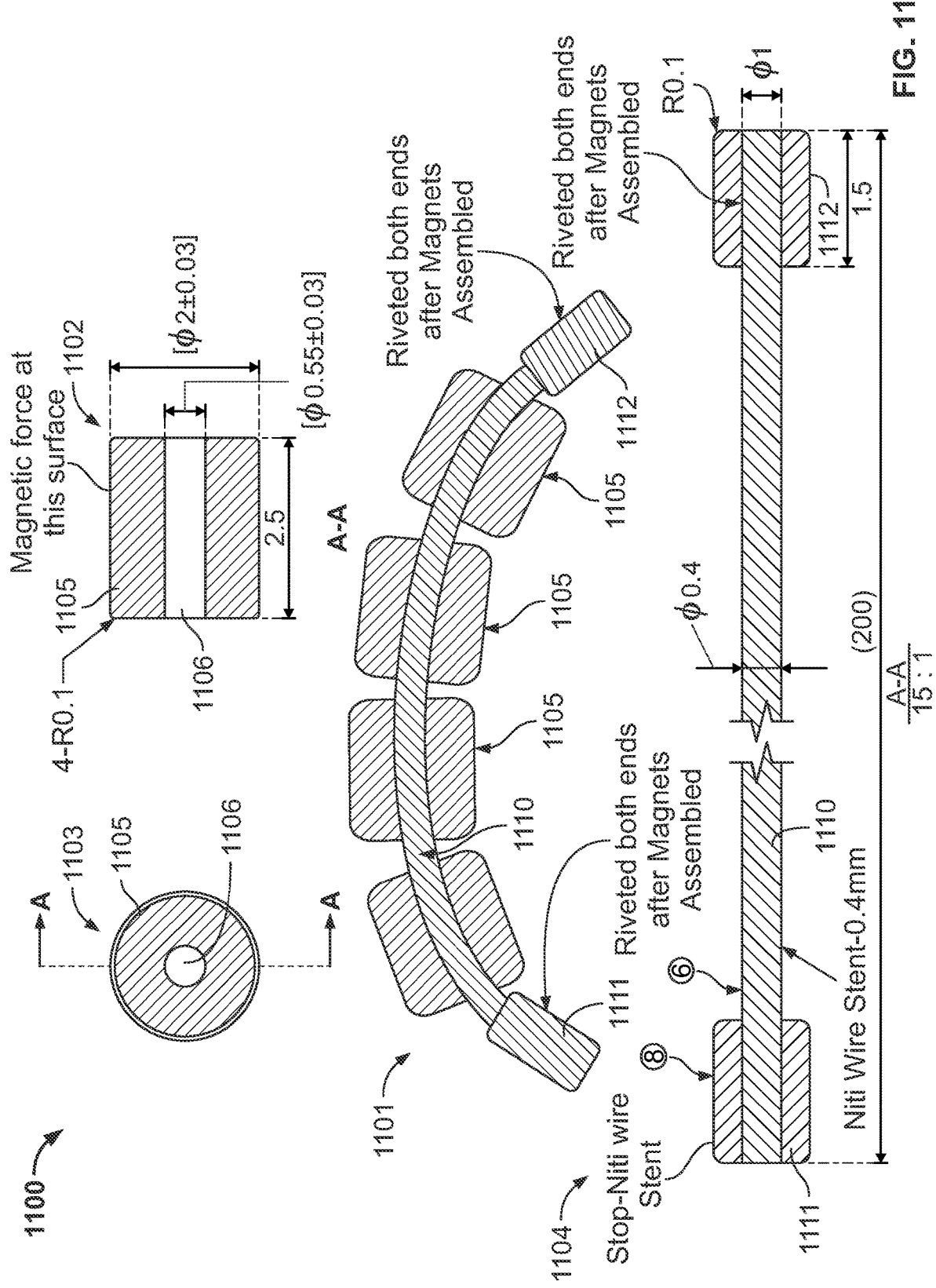
FIG. 11 illustrates a plurality of cross-sectional views of a dental implant, in accordance with some embodiments of the present specification.

FIG. 11 illustrates a plurality of cross-sectional views of a magnetic dental implant 1100, in accordance with some embodiments of the present specification. As shown in the cross-sectional view 1101 the dental implant 1100 comprises a plurality of magnetic elements 1105 strung over a wire 1110. As shown in the cross-sectional views 1102, 1103 each of the plurality of magnetic elements 1105 has a longitudinal through-formed channel or lumen 1106. The wire 1110 is inserted or threaded through the channel 1106 of each of the plurality of magnetic elements 1105 thereby stringing the elements 1105 over the wire 1110. In one embodiment, each element 1105 has a cylindrical shape with a longitudinal length of 2.5 mm and an outer diameter of 2±0.03 mm. The channel or lumen 1106 has a diameter of 0.55±0.03 mm. The magnetic elements are coated by a biocompatible material such as titanium or gold. The wire is made of a shape memory alloy such as Nitinol or stainless steel or any other biocompatible material.

As shown in the cross-sectional view 1104, in some embodiments, the wire 1110 has a total length of 200 mm and an outer diameter of 0.4 mm. In some embodiments, the wire 1110 comprises at least one of stainless steel, titanium, silk, PTFE, or Nitinol. The two ends of the wire 1110 are respectively plugged with first and second rivets 1111, 1112 after the plurality of magnetic elements 1105 are strung over the wire 1110. In one embodiment, each of the first and second rivets 1111, 1112 has a length of 1.5 mm and an outer diameter of 1 mm.

FIG. 12A illustrates a cross-sectional view of a magnetic dental implant 1200, in accordance with some embodiments of the present specification. The dental implant 1200 comprises a plurality of magnetic elements 1205 strung over a wire 1210. Each of the plurality of magnetic elements 1205 has a longitudinal through-formed channel or lumen 1206. The wire 1210 is inserted or threaded through the channel 1206 of each of the plurality of magnetic elements 1205 thereby stringing the elements 1205 over the wire 1110. The two ends of the wire 1210 are respectively plugged with first and second rivets 1211, 1212 after the plurality of magnetic elements 1205 are strung over the wire 1210.

In accordance with an embodiment, an articulating connector 1220 is incorporated at a position on the wire 1210. In an embodiment, the connector 1220 is positioned on the wire 1210 such that an equal number of elements 1205 are strung on either side of the connector 1220. FIG. 12B illustrates first, second, third, fourth and fifth configurations 1235, 1240, 1245, 1250, 1255 of the connector 1220.

Figure 12C:
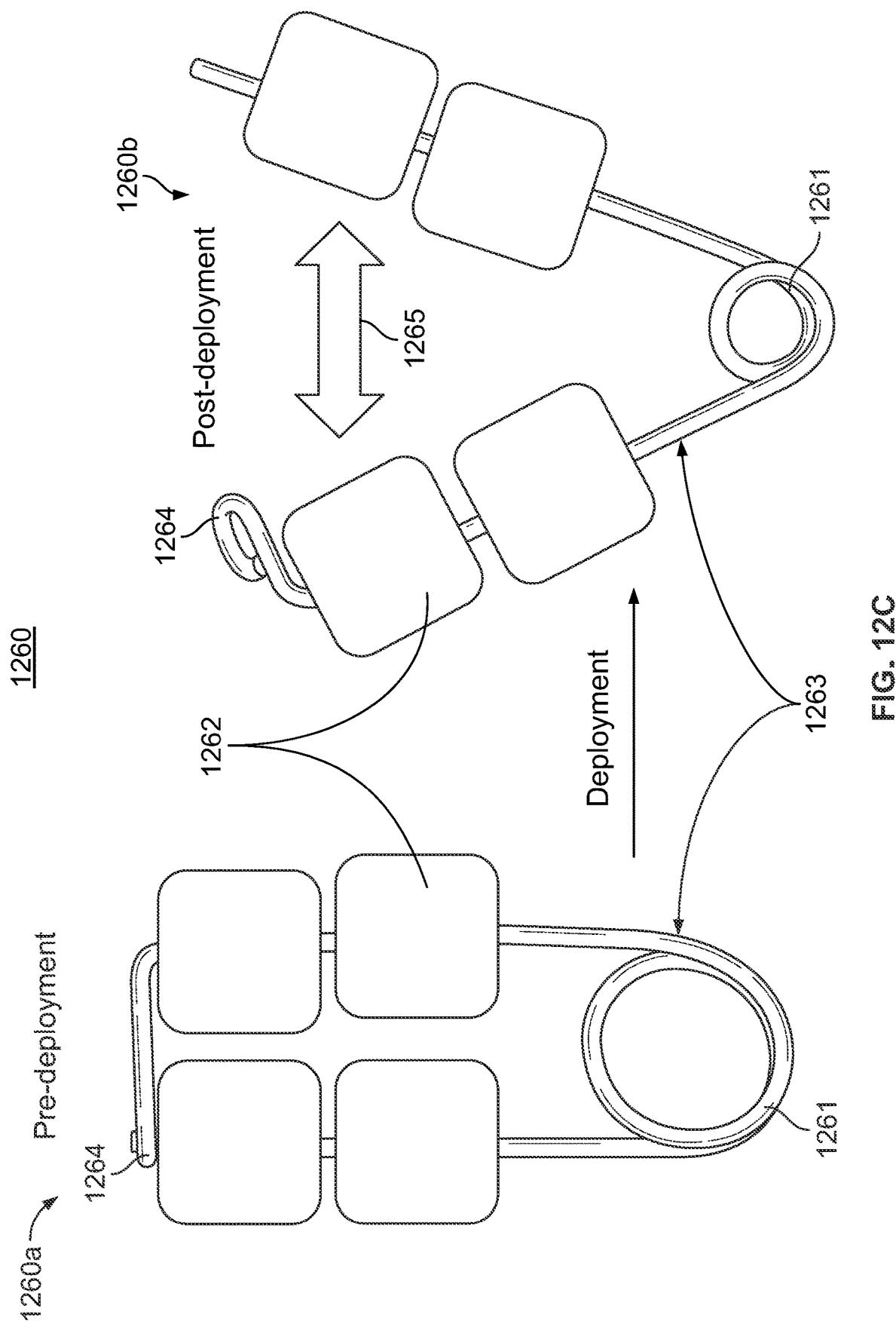
FIG. 12C illustrates compressed and expanded configurations of a device for treating obstructive sleep apnea comprising an articulating joint and magnets, in accordance with some embodiments of the present specification.

FIG. 12C illustrates compressed and expanded configurations of a device 1260 for treating obstructive sleep apnea comprising an articulating joint 1261 and magnets 1262, in accordance with some embodiments of the present specification. In some embodiments, the device 1260 is configured as a lingual implant which functions in concert with a dental implant in a fashion similar to the embodiments depicted in FIGS. 8A-9 to treat obstructive sleep apnea. In some embodiments, the device 1260 is configurable between a compressed, pre-deployment configuration 1260a for deployment through a catheter or trocar and an expanded, post-deployment configuration 1260b for implantation in a patient's lingual tissue. The device 1260 comprises a wire 1263 with a plurality of magnets 1262 connected to the wire 1263. In some embodiments, the wire 1263 is composed of a shape memory alloy, such as Nitinol. In some embodiments, the magnets 1262 are threaded on the wire 1263. The device 1260 includes a locking mechanism 1264 on an end of the device 1260 opposite an end comprising the articulating joint 1261. The locking mechanism 1264 is locked during delivery to help keep the device 1260 in the pre-deployment configuration 1260a and then unlocked upon delivery to allow the device 1260 to expand to the post-deployment configuration 1260b. Lateral force 1265, applied by one or more of the magnets 1262, shape memory properties of the wire 1263, or the articulating joint 1261, in the expanded post-deployment configuration 1260b helps anchor the device 1260 in the lingual tissue. Once the device 1260 is implanted, magnetic forces between the device 1260 and a corresponding dental implant pull the tongue forward to keep the patient's airway open to treat obstructive sleep apnea.

In various embodiments, the lingual implant is made of ferromagnetic core that is optionally covered with a biocompatible coating. In some embodiments, the lingual implant is made of biocompatible material. In some embodiments, the ferromagnetic core is one of a rare-earth magnet. In some embodiments, the biocompatible coating/material is one of Titanium, Gold, PEEK, Silicone or Teflon. In various embodiments, the lingual implant is appropriately shaped for patient fit and to minimize rejection or pressure necrosis. In various embodiments, the dimensions of the lingual implant are optimized to generate appropriate magnetic pull force. The pull force is ideally between 0.01 newton and 2 newtons. In some embodiments, the lingual implant incorporates at least one electrode, a capacitor, a battery or a pulse generator to generate and apply therapeutic electrical stimulation pulses to lingual tissue and nerves.

In various embodiments, the dental appliance has a ferromagnetic component that is optionally covered with a biocompatible coating. In some embodiments, the ferromagnetic component is one of a rare-earth magnet. In some embodiments, the biocompatible coating is one of Titanium, Gold, PEEK, Silicone or Teflon.

In various embodiments, the dental implant is appropriately shaped for patient fit. The strength and dimensions of the plurality of magnetic elements, of the dental implant, are optimized to generate appropriate and requisite pull force. The pull force is ideally between 0.01 newton and 2 newtons. The shape of the implant could be a sphere, a tube, a plate or any other atraumatic space optimized for housing in a dental appliance or implanted into lingual tissue. In some embodiments, each of the plurality of magnetic elements is covered with a biocompatible material such as, but not limited to, Titanium, Gold, PEEK, Silicone or Teflon. In some embodiments, each of the plurality of magnetic elements is made of a biocompatible material. In some embodiments, the dental implant incorporates a wireless pulse generator and a microprocessor to program and generate therapeutic electrical stimulations for wireless transmission to electrodes in the lingual implant. In some embodiments, the pulse generator is controlled to generate and customize stimulation pulses using a computing device such as, but not limited to, a mobile phone, PDA, laptop or a smart-watch. The computing device transmits controlling instructions to the pulse generator through wireless communication.

In some embodiments, a microphone is optionally incorporated in the lingual implant, dental implant or the dental appliance for recording the patient's breathing during sleep in order to drive/modulate stimulation and monitor the patient's progress to help optimize the dental appliance and the lingual bridge. In another embodiment, an accelerometer, an oximeter, or a capnometer is incorporated into the implant. The sensors can wirelessly send relevant information to a mobile phone, PDA, laptop or a smart-watch.

Figure 13B:
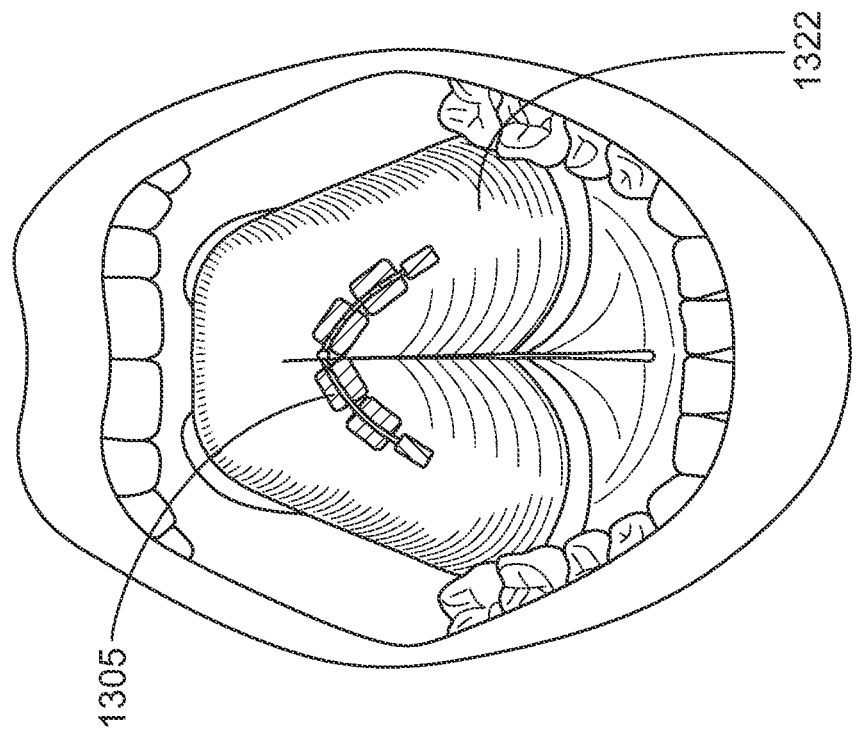
FIG. 13B illustrates another lingual implant positioned on a ventral surface of a patient's tongue, in accordance with some embodiments of the present specification.
Figure 13A:
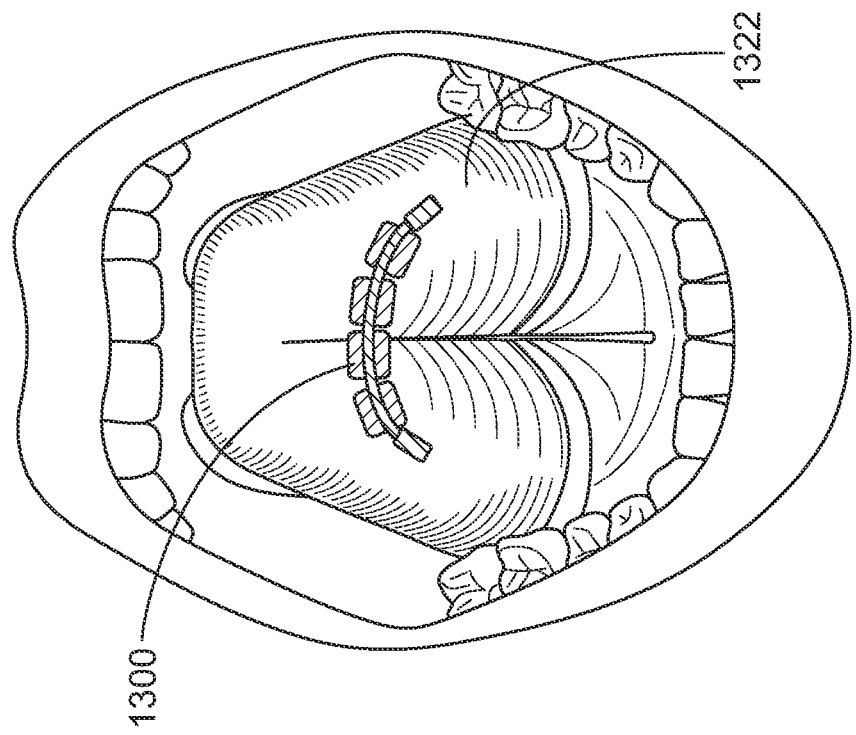
FIG. 13A illustrates a lingual implant positioned on a ventral surface of a patient's tongue, in accordance with some embodiments of the present specification.

FIG. 13A shows a dental implant 1300 similar to the implant 1100 shown in FIG. 11 implanted in a ventral surface of a tongue 1322 and 13B shows a dental implant 1305 similar to the implant 1200 shown in FIG. 12 implanted in a ventral surface of the tongue 1322.

In some embodiments, the lingual implants are a plurality of loose ferromagnetic particles coated with biocompatible coatings, designed to reduce or eliminate implant rejections and aid in implant fixation. The individual implant is sized to deliver through a hypodermic needle or a catheter and having enough mass to generate a magnetic force that will interfere with the movement of a tongue. The implants can be coated with anti-rejection agents or anti-microbial agents to reduce the chance of implant rejection.

Figure 15A:
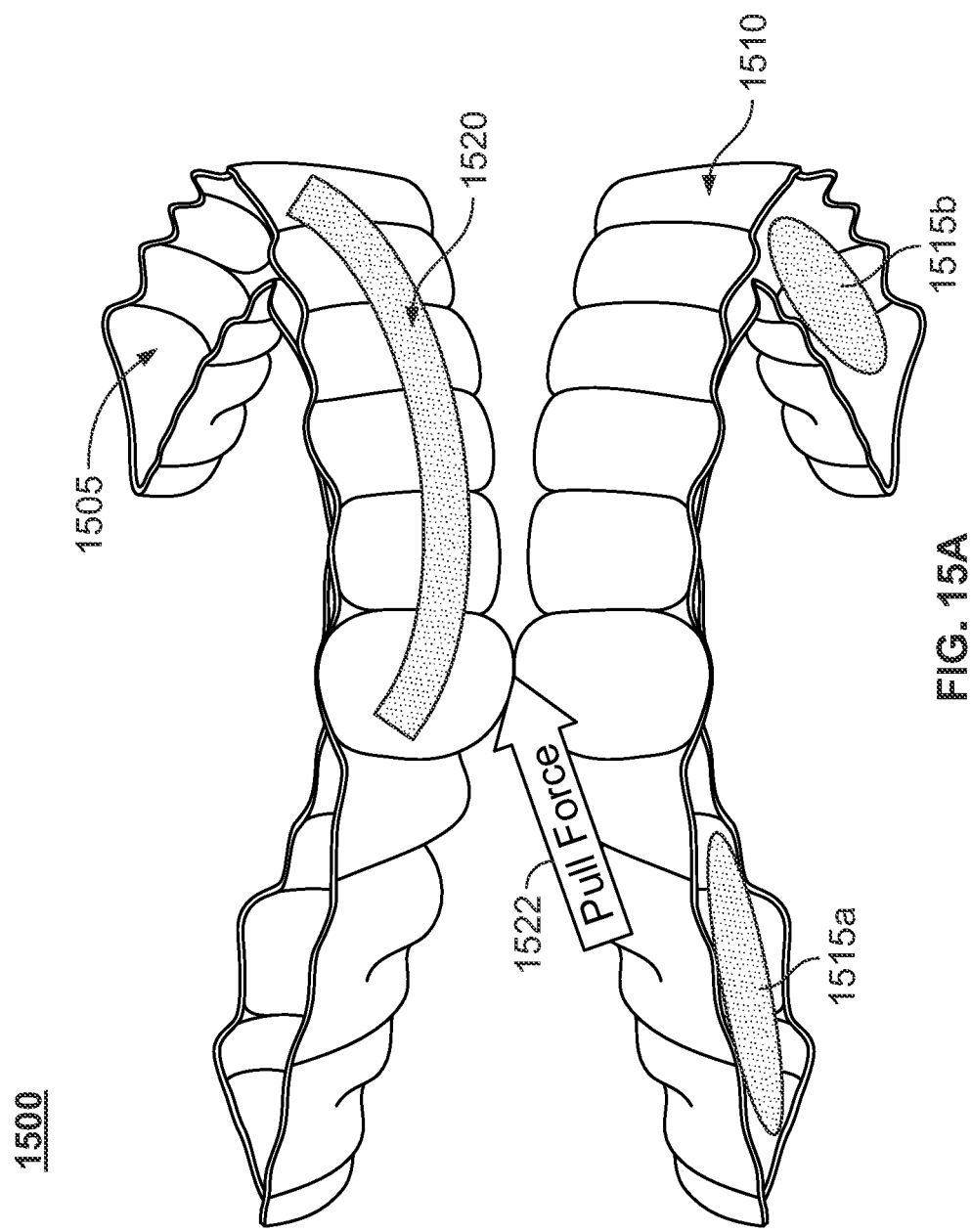
FIG. 15A shows elements of another device that work together through magnetic forces for treating obstructive sleep apnea, in accordance with some embodiments of the present specification.

FIG. 15A shows elements of a device 1500 that work together through magnetic forces for treating obstructive sleep apnea, in accordance with some embodiments of the present specification. The device 1500 comprises a first element 1505 configured as an upper jaw appliance custom shaped and sized to fix or grip onto and engage a patient's maxillary dental arcade, a second element 1510 configured as a lower jaw appliance custom shaped and sized to fix or grip onto and engage the patient's mandibular dental arcade, third elements, or right and left mandibular magnets 1515a, 1515b, incorporated or supported within the second element or lower jaw appliance 1510, and fourth elements, or maxillary magnet 1520, incorporated or supported within the first element or upper jaw appliance 1505. In embodiments, the fourth elements 1520 comprise one or more maxillary magnets 1520.

In some embodiments, the fourth elements or maxillary magnets 1520 are positioned in an anterior portion of the first element or the upper jaw appliance 1505 so as to lie proximate the patient's incisors while the third elements or right and left mandibular magnets 1515a, 1515b are positioned, respectively, in posterior right and left portions of the second element or the lower jaw appliance 1510 so as to respectively lie proximate the patient's right and left molars.

In some embodiments, the first and second elements 1505, 1510 are heat sensitive and may be molded to custom fit the patient's teeth. In some embodiments, the third and fourth elements 1515 (1515a, 1515b), 1520 are removable so they may be removed while the first and second elements 1505, 1510 are heated and molded to the patient's teeth.

During operation, when the device 1500 is positioned within the patient's oral cavity, a pull force 1522 is exerted by the fourth elements or maxillary magnets 1520 onto the right and left mandibular magnets 1515a, 1515b, thereby pulling the patient' lower jaw or mandible forward. In embodiments, strength of the magnets 1515a, 1515b and 1520 can be adjusted, hence modifying the pull force between the third elements or the right and left mandibular magnets 1515a, 1515b and the fourth elements or maxillary magnets 1520. In some embodiments, either the set of the right and left mandibular magnets 1515a, 1515b or the maxillary magnets 1520 comprise non-magnetic, ferromagnetic elements.

Figure 15B:
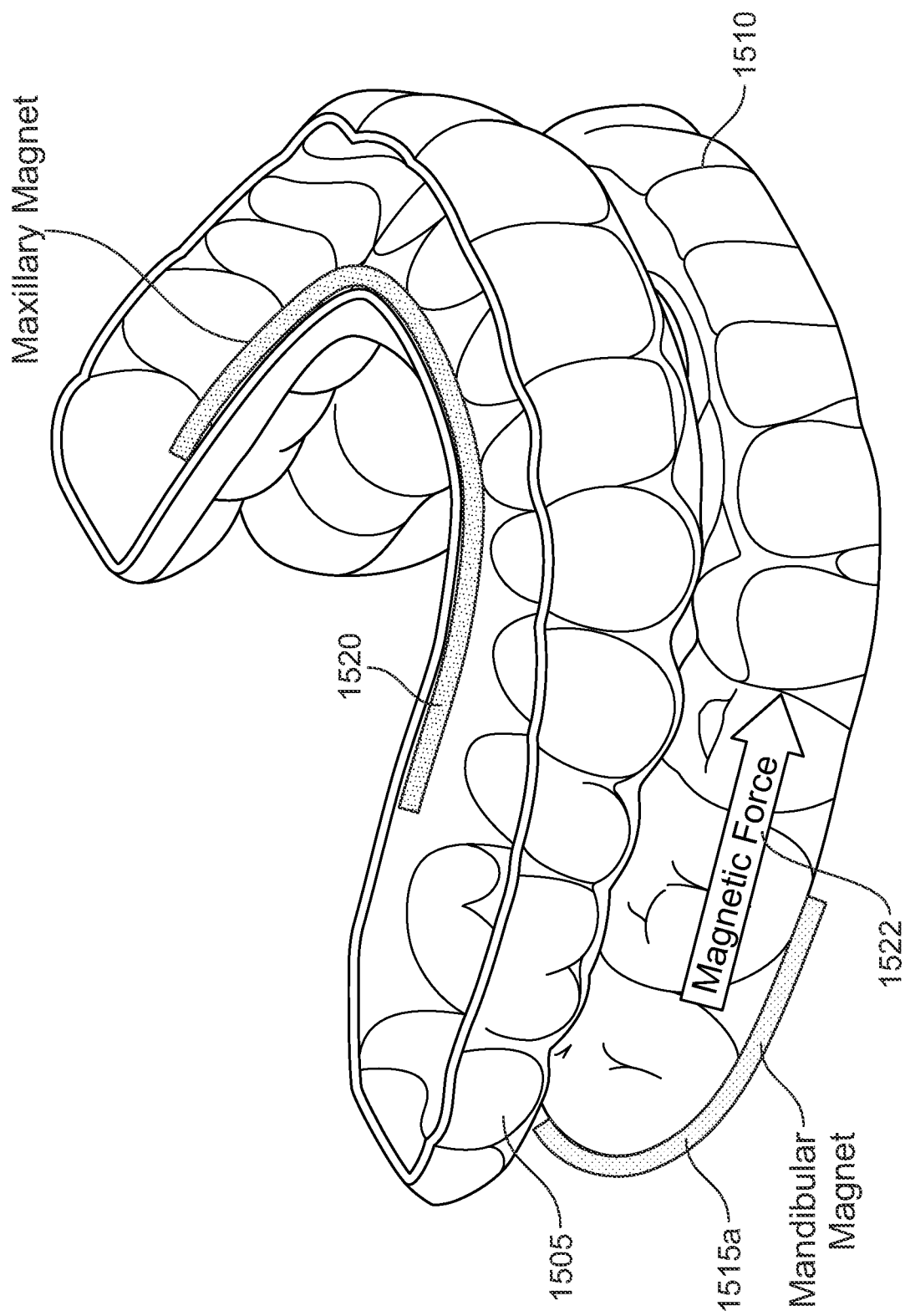
FIG. 15B is a perspective view showing a first positional configuration of mandibular and maxillary magnets within lower and upper jaw appliances, in accordance with some embodiments of the present specification.
Figure 15C:
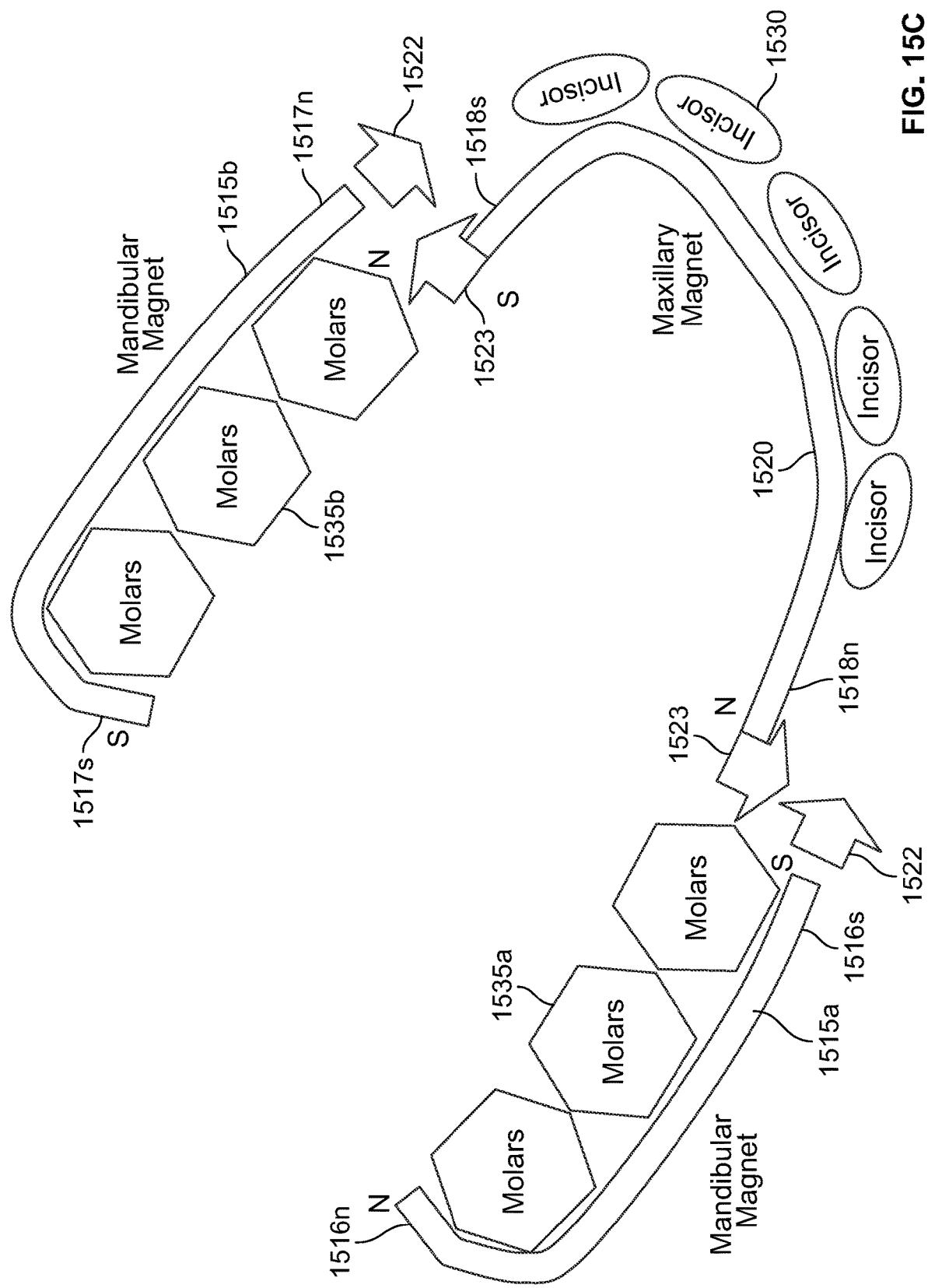
FIG. 15C is another view illustrating the first positional configuration of mandibular and maxillary magnets within lower and upper jaw appliances, in accordance with some embodiments of the present specification.

In some embodiments, as shown in FIGS. 15B and 15C, the maxillary magnets 1520 are positioned along a lingual surface of the upper jaw appliance 1505 so as to lie proximate the patient's incisors 1530 while the right and left mandibular magnets 1515a, 1515b are positioned respectively along right and left buccal surfaces of the lower jaw appliance 1510 so as to lie proximate the patient's right and left molars 1535a, 1535b. This positional configuration of the magnets 1515a, 1515b and 1520 creates forward force vectors 1522 which pull the patient's lower jaw or mandible forward, while the lateral force vectors 1523 cancel each other out. In embodiments, strength of the magnets 1515a, 1515b and 1520 may be adjusted to modify the forward force vectors 1522 in order to create a desired therapeutic effect without being uncomfortable to the patient. In some embodiments, as depicted in FIG. 15C, the right mandibular magnet 1515a is configured with a N pole 1516n positioned toward a back or posterior portion of the patient's mouth and a S pole 1516s positioned toward a front or anterior portion of the patient's mouth, the left mandibular magnet 1515b is configured with a N pole 1517n positioned toward a front or anterior portion of the patient's mouth and a S pole 1517s positioned toward a back or posterior portion of the patient's mouth, and the maxillary magnet or magnets 1520 are positioned with a N pole 1518n positioned toward a right side of the patient's mouth and a S pole 1518s positioned toward a left side of the patient's mouth.

Figure 15D:
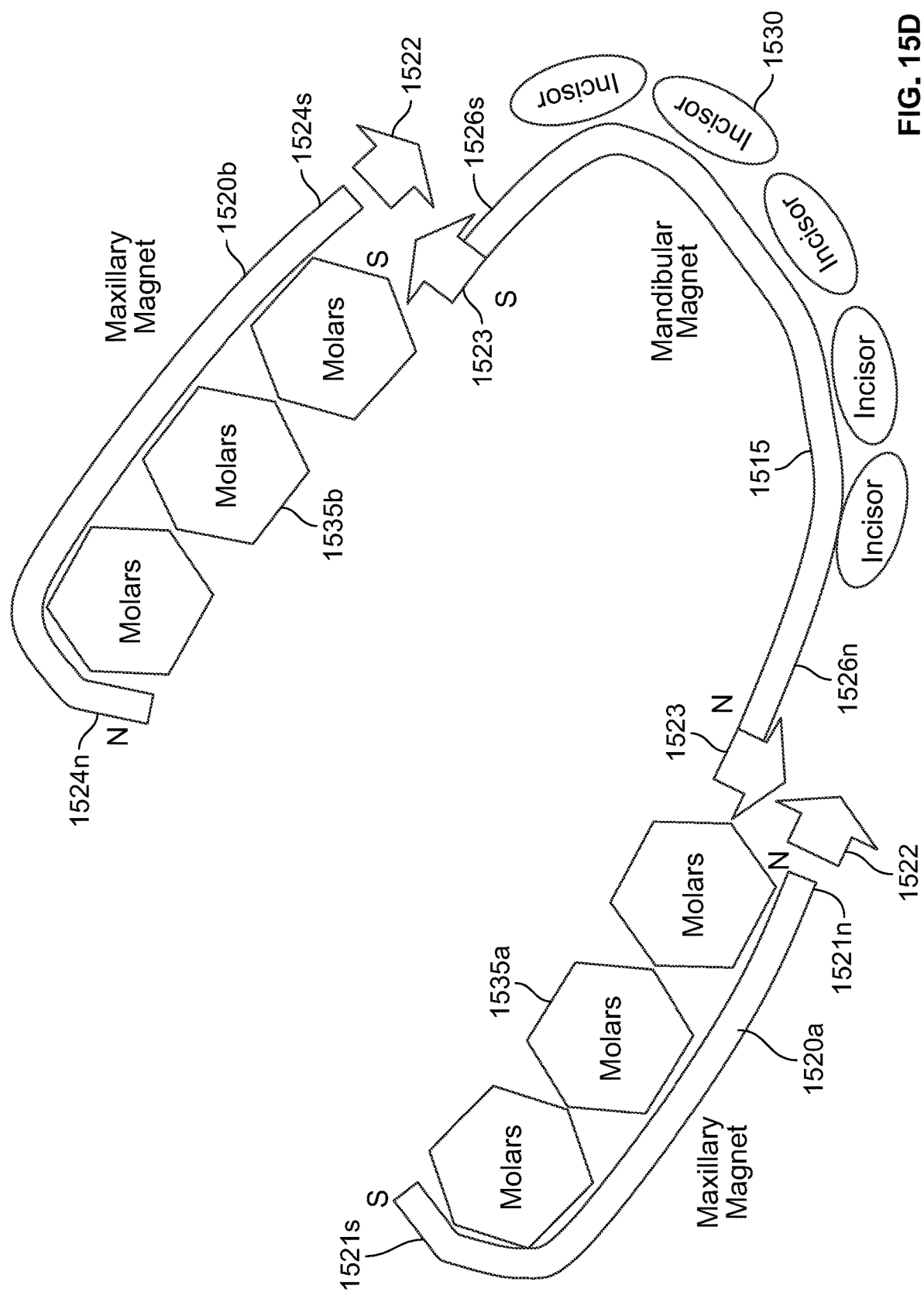
FIG. 15D illustrates a second positional configuration of mandibular and maxillary magnets within lower and upper jaw appliances, in accordance with some embodiments of the present specification.

In some embodiments, as shown in FIG. 15D, right and left maxillary magnets 1520a, 1520b are positioned along the buccal surface of the upper jaw appliance 1505 so as to respectively lie proximate the patient's right and left molars 1535a, 1535b while the mandibular magnets 1515 are positioned along the lingual surface of the lower jaw appliance 1510 so as to lie proximate the patient's incisors 1530. This positional configuration of the magnets 1515, 1520a, and 1520b creates forward force vectors 1522 which push the patient's lower jaw or mandible forward, while the lateral force vectors 1523 cancel each other out. In embodiments, strength of the magnets 1515, 1520a, and 1520b may be adjusted to modify the forward force vectors 1522 in order to create a desired therapeutic effect without being uncomfortable to the patient. It should be appreciated that the push force decreases as the distance between the magnets 1515 and 1520a, 1520b increases. In some embodiments, as depicted in FIG. 15D, the right maxillary magnet 1520a is configured with a N pole 1521n positioned toward a front or anterior portion of the patient's mouth and a S pole 1521s positioned toward a back or posterior portion of the patient's mouth, the left mandibular magnet 1520b is configured with a N pole 1524n positioned toward a back or posterior portion of the patient's mouth and a S pole 1524s positioned toward a front or anterior portion of the patient's mouth, and the maxillary magnet or magnets 1515 are positioned with a N pole 1526n positioned toward a right side of the patient's mouth and a S pole 1526s positioned toward a left side of the patient's mouth.

Figure 15E:
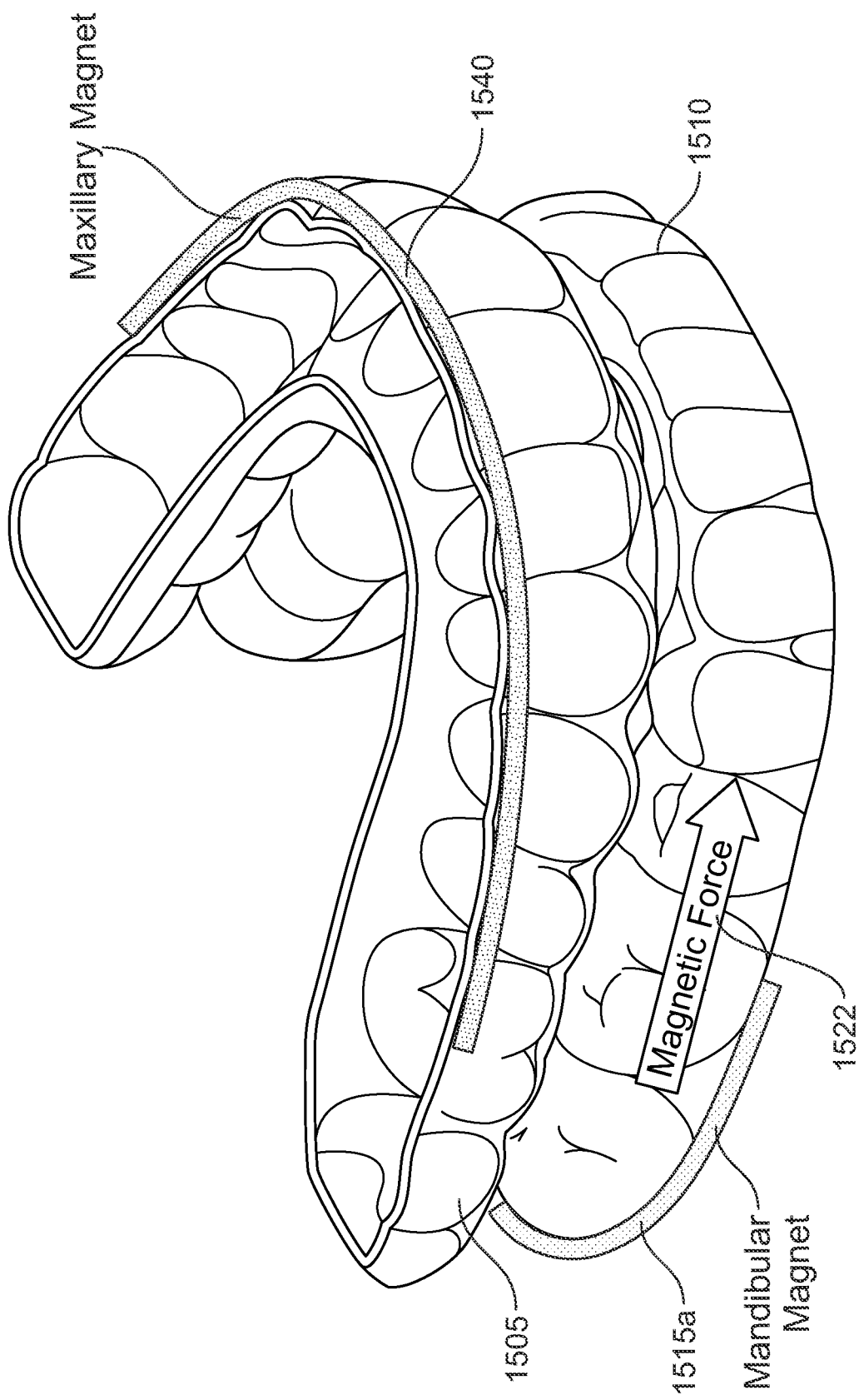
FIG. 15E is a perspective view showing a third positional configuration of mandibular and maxillary magnets within lower and upper jaw appliances, in accordance with some embodiments of the present specification.
Figure 15F:
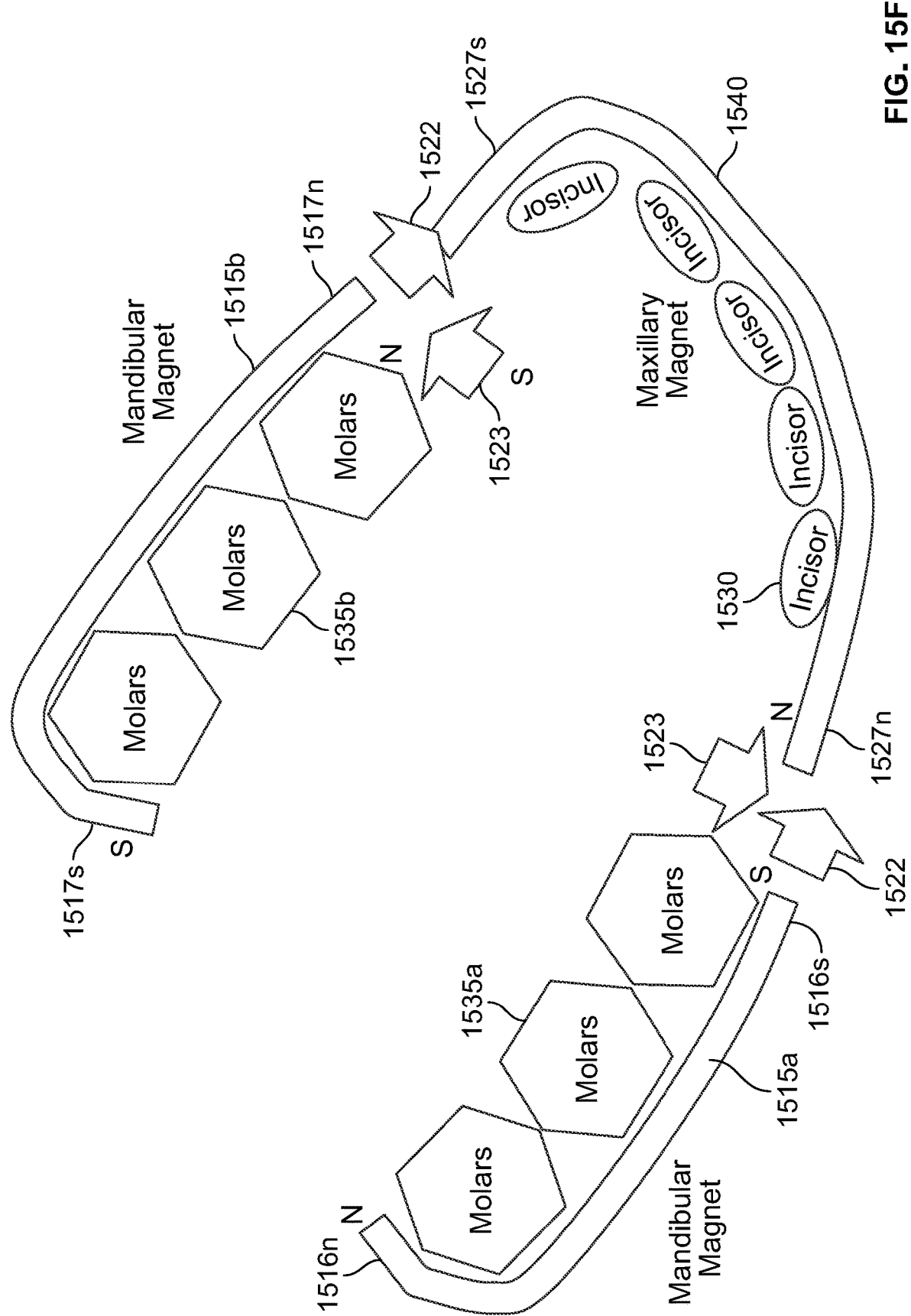
FIG. 15F is another view illustrating the third positional configuration of mandibular and maxillary magnets within lower and upper jaw appliances, in accordance with some embodiments of the present specification.

In some embodiments, the maxillary magnets as well as the mandibular magnets are positioned along the same surface, buccal or lingual, of the upper and lower jaw appliances. In some embodiments, as shown in FIGS. 15E and 15F, the maxillary magnets 1540 are positioned along the buccal surface of the upper jaw appliance 1505 so as to lie proximate the patient's incisors 1530 while the right and left mandibular magnets 1515a, 1515b are respectively positioned along the buccal surface of the upper jaw appliance 1505 so as to respectively lie proximate the patient's right and left molars 1535a, 1535b. This positional configuration of the magnets 1515a, 1515b, and 1540 creates forward force vectors 1522 which pull the patient's lower jaw or mandible forward, while the lateral force vectors 1523 cancel each other out. In embodiments, strength of the magnets 1515a, 1515b, and 1540 may be adjusted to modify the forward force vectors 1522 in order to create a desired therapeutic effect without being uncomfortable to the patient. In some embodiments, as depicted in FIG. 15F, the right mandibular magnet 1515a is configured with a N pole 1516n positioned toward a back or posterior portion of the patient's mouth and a S pole 1516s positioned toward a front or anterior portion of the patient's mouth, the left mandibular magnet 1515b is configured with a N pole 1517n positioned toward a front or anterior portion of the patient's mouth and a S pole 1517s positioned toward a back or posterior portion of the patient's mouth, and the maxillary magnet or magnets 1540 are positioned with a N pole 1527n positioned toward a right side of the patient's mouth and a S pole 1527s positioned toward a left side of the patient's mouth.

In alternate embodiments, as shown in FIG. 15G, right and left maxillary magnets 1520a, 1520b are positioned along the buccal surface of the upper jaw appliance 1505 so as to respectively lie proximate the patient's right and left molars 1535a, 1535b while the mandibular magnets 1545 are also positioned along the buccal surface of the lower jaw appliance 1510 so as to lie proximate the patient's incisors 1530. This positional configuration of the magnets 1545, 1520a, and 1520b creates forward force vectors 1522 which push the patient's lower jaw or mandible forward, while the lateral force vectors 1523 cancel each other out. In embodiments, strength of the magnets 1545, 1520a, and 1520b may be adjusted to modify the forward force vectors 1522 in order to create a desired therapeutic effect without being uncomfortable to the patient. It should be appreciated that the push force decreases as the distance between the magnets 1545 and 1520a, 1520b increases. In some embodiments, as depicted in FIG. 15G, the right maxillary magnet 1520a is configured with a N pole 1521n positioned toward a front or anterior portion of the patient's mouth and a S pole 1521s positioned toward a back or posterior portion of the patient's mouth, the left mandibular magnet 1520b is configured with a N pole 1524n positioned toward a back or posterior portion of the patient's mouth and a S pole 1524s positioned toward a front or anterior portion of the patient's mouth, and the maxillary magnet or magnets 1545 are positioned with a N pole 1528n positioned toward a right side of the patient's mouth and a S pole 1528s positioned toward a left side of the patient's mouth.

In embodiments that use magnets to treat sleep apnea, magnetic field shields can be used to direct the magnetic field preferably into the patient's oral cavity and minimize the spread of magnetic field outside the patient's oral cavity in order to create appropriate force vectors. The magnetic shielding could be effectuated by using layers of Mu metal coating. Other materials for magnetic shielding include Co-NETIC®, supermalloy, supermumetal, NILOMAG®, sanbold, molybdenum permalloy, Sendust, M-1040, Hipernom®, HyMu 80 and Amumetal. Pyrolytic graphite can be used for its magnetic field exclusion properties.

Therapeutic Objectives

In various embodiments, the dental appliances or devices, as described above, provide and/or enable one or more of the following therapeutic goals:

Reduction in an apnea-hypopnea index by 5% relative to a pre-treatment apnea-hypopnea index;
Reduction in a number of apnea events by 2 events/hour relative to a pre-treatment number of apnea events;
Improved daytime sleepiness as assessed by the Epworth Sleepiness Scale by 5% or 1 point relative to pre-treatment daytime sleepiness as assessed by the Epworth Sleepiness Scale;
Improved systolic and diastolic blood pressure by 2 mm Hg and 1 mm Hg, respectively, relative to pre-treatment systolic and diastolic blood pressure;
Improved sleep-related quality of life by 5% relative to pre-treatment sleep-related quality of life, as determined using surveys or visual analog scales designed to assess a patient's perspective of his or her quality of life;
Improvement in subjective and objective sleepiness by 5% relative to pre-treatment subjective and objective sleepiness, as determined using surveys or visual analog scales designed to assess a patient's perspective of his or her sleep quality or as determined using respiratory, EEG, SpO$_2$, pulse rate, blood pressure, or other sensors configured to determine a state or extent of sleep;
Improvement cognitive function or depression by 5% relative to pre-treatment quality of life, cognitive function, and depression, as determined using surveys or visual analog scales designed to assess a patient's perspective of his or her mental or emotional state;
Improving oxyhemoglobin saturation by 1% relative to pre-treatment oxyhemoglobin saturation;
Improving snoring by 5% relative to pre-treatment snoring, as determined by a sleep studies performed both before and after treatment;
Improving arousal index by 5% relative to a pre-treatment arousal index
Decreasing a number of arousal events by 1 event/hour relative to a pre-treatment number of arousal events
Complete resolution of OSA, defined as an apnea-hypopnea index (AHI)<5 events per hour during treatment occurring in 5% of patients
Change in multiple sleep latency test (MSLT) and the maintenance of wakefulness test (MWT), Oxford SLEep Resistance (OSLER) test, Stanford Sleepiness Scale (SSS) subjectively quantify sleepiness by 5% relative to pretreatment scores.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

I claim:

1. A device for treating obstructive sleep apnea in a patient, comprising:
a lower jaw appliance configured to engage the patient's mandibular dental arcade;
an upper jaw appliance configured to engage the patient's maxillary dental arcade; and
a first telescoping connector comprising a first member and a second member, wherein the first member and second member are configured to telescope relative to each other to thereby modulate a length of the first telescoping connector, wherein the first member is attached to at least one of the lower jaw appliance or upper jaw appliance, wherein the second member is attached to at least one of the lower jaw appliance or upper jaw appliance and wherein the first member and second member are not both attached to the lower jaw appliance or the upper jaw appliance, wherein a first magnet is positioned at a first end of the first telescoping connector and inside the first member, wherein a second magnet is positioned at a second end of the first telescoping connector, opposing the first end and inside the second member, and wherein the first magnet and second magnet are oriented such that like polarities face each other and thereby generate a repulsive force configured to push the first end away from the second end.

2. The device of claim 1, further comprising a second telescoping connector comprising a third member and a fourth member, wherein the third member is configured to at least partially cover the fourth member, wherein the third member and fourth member are configured to telescope relative to each other to thereby modulate a length of the second telescoping connector, wherein the third member is attached to at least one of the lower jaw appliance or upper jaw appliance, wherein the fourth member is attached to at least one of the lower jaw appliance or upper jaw appliance, wherein the third member and fourth member are not both attached to a same one of the lower jaw appliance or the upper jaw appliance, wherein a fourth magnet is positioned at a first end of the second telescoping connector and inside the third member, wherein a fifth magnet is positioned at a second end of the second telescoping connector, opposing the first end, and inside the fourth member.

3. The device of claim 2, wherein the fourth magnet and fifth magnet are oriented such that like polarities face each other and thereby generate a repulsive force configured to push the first end of the second telescoping connector away from the second end of the second telescoping connector.

4. The device of claim 3, further comprising a sixth magnet positioned between the fourth magnet and the fifth magnet, wherein the fourth magnet and sixth magnet are oriented such that like polarities face each other and thereby generate a repulsive force configured to push the fourth magnet and sixth magnet away from each other and wherein the fifth magnet and sixth magnet are oriented such that like polarities face each other and thereby generate a repulsive force configured to push the fifth magnet and sixth magnet away from each other.

5. The device of claim 1, further comprising a second telescoping connector comprising a third member and a fourth member, wherein the third member and fourth member are configured to telescope relative to each other to thereby modulate a length of the second telescoping connector, wherein the third member is attached to at least one of the lower jaw appliance or upper jaw appliance, wherein the fourth member is attached to at least one of the lower jaw appliance or upper jaw appliance and wherein the third member and fourth member are not both attached to a same one of the lower jaw appliance or the upper jaw appliance.

6. The device of claim 5, wherein the first telescoping connector is configured to be positioned on a left buccal surface of the patient's dental arcades.

7. The device of claim 5, wherein the second telescoping connector is configured to be positioned on a right buccal surface of the patient's dental arcades.

8. The device of claim 5, wherein the first member is a partially hollow arm configured to slidably receive the second member and wherein the third member is a partially hollow arm configured to slidably receive the fourth member.

9. The device of claim 5, wherein the second member is configured to slide into, and out of, the first member in response to an amount of movement of the patient's mandibular dental arcade relative to an amount of movement of the patient's maxillary dental arcade and wherein the fourth member is configured to slide into, and out of, the third member in response to an amount of movement of the patient's mandibular dental arcade relative to an amount of movement of the patient's maxillary dental arcade.

10. The device of claim 1, wherein the first member and second member are physically coupled by a sliding joint.

11. The device of claim 10, wherein the sliding joint comprises a U-shaped groove configured to enable the first member and the second member to be disconnected and connected.

12. The device of claim 1, further comprising at least one pulse generator and at least one electrode, wherein the at least one pulse generator and at least one electrode are electrically coupled and physically coupled to the lower jaw appliance.

13. The device of claim 12, wherein the at least one pulse generator is configured to drive the at least one electrode to apply stimulation to at least one of the patient's genioglossus, the patient's hyoglossus muscle, or to a nerve supplying the patient's genioglossus or hyoglossus muscle.

14. The device of claim 1, further comprising a third magnet positioned between the first magnet and the second magnet, wherein the first magnet and third magnet are oriented such that like polarities face each other and thereby generate a repulsive force configured to push the first magnet and third magnet away from each other and wherein the second magnet and third magnet are oriented such that like polarities face each other and thereby generate a repulsive force configured to push the second magnet and third magnet away from each other.

15. The device of claim 1, further comprising a lingual bridge coupled to the lower jaw appliance and configured to lie over, and apply pressure to, the patient's tongue, wherein such applied pressure is sufficient to prevent the patient's tongue from impeding airflow in the patient's oropharynx.

16. A device for treating obstructive sleep apnea in a patient, comprising:
a lower jaw appliance configured to engage the patient's mandibular dental arcade;
an upper jaw appliance configured to engage the patient's maxillary dental arcade;
a first telescoping connector comprising a first member connected to the lower jaw appliance and a second member connected to the upper jaw appliance, wherein the first member and second member are configured to slidably telescope relative to each other to thereby modulate a length of the first telescoping connector;
a first set of magnets positioned within the first telescoping connector such that a first portion of the first set of magnets is oriented relative to a second portion of the first set of magnets such that like polarities face each other and generate a repulsive force configured to push opposing ends of the first telescoping connector away from each other;
a second telescoping connector comprising a third member connected to the lower jaw appliance and a fourth member connected to the upper jaw appliance, wherein the third member and fourth member are configured to slidably telescope relative to each other to thereby modulate a length of the second telescoping connector;
a second set of magnets positioned within the second telescoping connector such that a first portion of the second set of magnets is oriented relative to a second portion of the second set of magnets such that like polarities face each other and generate a repulsive force configured to push opposing ends of the second telescoping connector away from each other.

17. The device of claim 16, wherein the first telescoping connector is configured to be positioned on a left buccal surface of the patient's dental arcades.

18. The device of claim 17, wherein the second telescoping connector is configured to be positioned on a right buccal surface of the patient's dental arcades.

19. The device of claim 16, wherein the first member is a partially hollow arm configured to slidably receive the second member and wherein the third member is a partially hollow arm configured to slidably receive the fourth member.

20. The device of claim 16, wherein the second member is a partially hollow arm configured to slidably receive the first member and wherein the fourth member is a partially hollow arm configured to slidably receive the third member.

21. The device of claim 16, wherein the second member is configured to slide into, and out of, the first member in response to an amount of movement of the patient's mandibular dental arcade relative to an amount of movement of the patient's maxillary dental arcade and wherein the fourth member is configured to slide into, and out of, the third member in response to an amount of movement of the patient's mandibular dental arcade relative to an amount of movement of the patient's maxillary dental arcade.

22. The device of claim 16, wherein the first member is configured to slide into, and out of, the second member in response to an amount of movement of the patient's mandibular dental arcade relative to an amount of movement of the patient's maxillary dental arcade and wherein the third member is configured to slide into, and out of, the fourth member in response to an amount of movement of the patient's mandibular dental arcade relative to an amount of movement of the patient's maxillary dental arcade.

* * * * *